US006514693B1

(12) United States Patent
Lansdorp

(10) Patent No.: US 6,514,693 B1
(45) Date of Patent: *Feb. 4, 2003

(54) METHOD FOR DETECTING MULTIPLE COPIES OF A REPEAT SEQUENCE IN A NUCLEIC ACID MOLECULE

(75) Inventor: Peter Lansdorp, Vancouver (CA)

(73) Assignee: Tetramerics Biotechnology, Inc., Vancouver (CA)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/730,635

(22) Filed: Oct. 11, 1996

Related U.S. Application Data

(60) Provisional application No. 60/005,590, filed on Oct. 12, 1995, and provisional application No. 60/007,616, filed on Nov. 28, 1995.

(51) Int. Cl.$^7$ ............................. C12Q 1/68; C12M 1/34; C12N 5/00; C07H 21/04
(52) U.S. Cl. ........................... 435/6; 435/7.1; 435/183; 435/288.3; 435/325; 436/164; 536/23.5; 536/24.31
(58) Field of Search ..................... 435/6, 7.1, 91.1, 435/183, 810, 325; 436/513, 800, 164; 536/24.3, 24.31, 23.5; 935/77, 78

(56) References Cited

U.S. PATENT DOCUMENTS

| 5,464,945 | A | * | 11/1995 | Reynolds et al. | ......... | 536/24.31 |
| 5,489,508 | A | * | 2/1996 | West et al. | ...................... | 435/6 |
| 5,830,644 | A | * | 11/1998 | West et al. | ...................... | 435/6 |
| 5,834,193 | A | | 11/1998 | Kozlowski et al. | | |
| 5,840,478 | A | * | 11/1998 | Patterson et al. | .............. | 435/5 |
| 5,888,734 | A | | 3/1999 | Cremer et al. | | |
| 5,985,563 | A | | 11/1999 | Hyldig-Nielsen et al. | | |

FOREIGN PATENT DOCUMENTS

| WO | WO86/05518 | 9/1986 |
| WO | WO92/20702 | 11/1992 |
| WO | WO92/20703 | 11/1992 |
| WO | WO93/24652 | 12/1993 |
| WO | WO93/25706 | 12/1993 |
| WO | WO94/25477 | 11/1994 |
| WO | WO95/01369 | 1/1995 |
| WO | WO95/01370 | 1/1995 |
| WO | WO95/13382 | 5/1995 |

OTHER PUBLICATIONS

Boffa et al. "Isolation of active genes containing CAG repeats by DNA strand invasion by a peptide nucleic acid" Proc. Natl. Acad. Sci., USA. 92:1901–1905, Mar. 1995.*

M. Egholm et al, "PNA Hybridizes to Complementary Oligonucleotides Obeying the Watson–Crick Hydrogen–Bonding Rules", Nature, 365:566–568 (Oct. 7, 1993) [Egholm I].

M. Egholm et al, "Peptide Nucleic Acids (PNA). Oligonucleotide Analogues with an Achiral Peptide Backbone", J. Am. Chem. Soc., 114:1895–1897 (1992) [Egholm II].

M. Egholm et al, "Recognition of Guanine and Adenine in DNA by Cytosine and Thymine Containing Peptide Nucleic Acids (PNA)", J. Am. Chem. Soc., 114:9677–9678 (1992) [Egholm III].

M. Egholm et al, "Peptide Nucleic Acids Containing Adenine or Guanine Recognize Thymine and Cytosine in Complementary DNA Sequences", J. Chem. Soc. Chem. Commun., pp. 800–801 (1993) [Egholm IV].

O. Buchardt et al, "Peptide Nucleic Acids and their Potential Applications in Biotechnology", TIBTECH, 11:384–386 (Sep., 1993).

P. Lansdorp et al, "Heterogeneity in Telomere Length of Human Chromosomes", Human Molecular Genetics, 5(5):685–691 (1996).

P. Nielsen et al, "Peptide Nucleic Acid (PNA). A DNA Mimic with a Peptide Backbone", Bioconjugate Chem., 5:3–7 (1994).

M. Pluskal et al, "Peptide Nucleic Acid Probes and their Application in DNA and RNA Blot Hybridization Analysis", FASEB Journal, Poster 35, Abstract, American Society for Biochemistry and Molecular Biology, 85th Annual Meeting, Washington, DC (May 21–25, 1994).

R. Allshire et al, "Human Telomeres Contain at Least Three Types of G–rich Repeat Distributed Non–Randomly", Nucl. Acids Res., 17(12):4611–4627 (1989).

R. Allsopp et al, "Telomere Length Predicts Replicative Capacity of Human Fibroblasts", Proc. Natl. Acad. Sci. USA, 89:10114–10118 (Nov., 1992).

E. Blackburn, "Structure and Function of Telomeres", Nature, 350:569–572 (Apr. 18, 1991) [Blackburn I].

E. Blackburn, "Telomeres: No End in Sight", Cell, 77:621–623 (Jun. 3, 1994) [Blackburn II].

(List continued on next page.)

Primary Examiner—Stephanie W. Zitomer
(74) Attorney, Agent, or Firm—Gibbons, Del Deo, Dolan, Griffinger & Vecchione

(57) ABSTRACT

A method for detecting or quantitating multiple copies of a repeat sequence in a nucleic acid molecule involving treating the nucleic acid molecule with a probe which is a nucleic acid analogue which is capable of hybridizing to the repeat sequence in the nucleic acid molecule and which is labelled with a detectable substance. The nucleic acid molecule is treated with the probe under conditions permitting the probe to hybridize to the repeat sequences in the nucleic acid molecule. Probe hybridized to complementary repeat sequences is identified in the nucleic acid molecule by directly or indirectly detecting the detectable substance. The method is preferably used for quantitating multiple copies of a repeat sequence in a nucleic acid molecule, preferably a telomere or centromere repeat sequence. Novel probes for use in the method of the invention and kits are described.

19 Claims, 6 Drawing Sheets

OTHER PUBLICATIONS

W. Carrington et al, "Superresolution Three–Dimensional Images of Fluorescence in Cells with Minimal Light Exposure", Science, 268:1483–1487 (Jun. 9, 1995).

C. Counter et al, "Telomere Shortening Associated with Chromosome Instability is Arrested in Immortal Cells Which Express Telomerase Activity", EMBO J., 11(5):1921–1929 (1992).

C. Greider et al, "Identification of a Specific Telomere Terminal Transferase Activity in Tetrahymena Extracts", Cell, 43:405–413 (Dec., 1985).

C. Harley et al, "Telomeres Shorten During Ageing of Human Fibroblasts", Nature, 345:458–460 (May 31, 1990) [Harley I].

C. Harley, "Telomere Loss: Mitotic Clock or Genetic Time Bomb?", Mutation Research, 256:271–282 (1991) [Harley II].

C. Harley et al, "The Telomere Hypothesis of Cellular Aging", Exp. Gerontol., 27:375–382 (1992) [Harley III].

N. Hastie et al, "Telomere Reduction in Human Colorectal Carcinoma and with Ageing", Nature, 346:866–868 (Aug. 30, 1990).

Y. Hiraoka et al, "Determination of Three–Dimensional Imaging Properties of a Light Microscope System", Biophys. J., 57:325–333 (Feb., 1990).

D. Howard et al, "Lymphocyte Function–Associated Antigen (LFA–1) is Involved in B Cell Activation", J. Immunol., 136(11):4013–4018 (Jun. 1, 1986).

N. Kim et al, "Specific Association of Human Telomerase Activity with Immortal Cells and Cancer", Science, 266:2011–2015 (Dec. 23, 1994).

J. Lindsey et al, "In vivo Loss of Telomeric Repeats with Age in Humans", Mutation Research, 256:45–48 (1991).

V. Lundblad et al, "A Mutant with a Defect in Telomere Elongation Leads to Senescence in Yeast", Cell, 57:633–643 (May 19, 1989).

P. Meltzer et al, "Telomere Capture Stabilizes Chromosome Breakage", Nature Genetics, 4:252–255 (Jul., 1993).

J. Meyne et al, "In Situ Hybridization Using Synthetic Oligomers as Probes for Centromere and Telomere Repeats", Methods in Molecular Biology, 33:63–74 (1994).

G. Morin, "The Human Telomere Terminal Transferase Enzyme is a Ribonucleoprotein that Synthesizes TTAGGG Repeats", Cell, 59:521–529 (Nov. 3, 1989).

R. Moyzis et al, "A Highly Conserved Repetitive DNA Sequence (TTAGGG)n, Present at the Telomeres of Human Chromosomes", Proc. Natl. Acad. Sci. USA, 85:6622–6626 (Sep., 1988).

P. Nederlof et al, "Quantification of Fluorescence in situ Hybridization Signals by Image Cytometry", Cytometry, 13:846–852 (1992) [Nederlof I].

P. Nederlof et al, "Fluorescence Ratio Measurements of Double–Labeled Probes for Multiple in situ Hybridization by Digital Imaging Microscopy", Cytometry, 13:839–845 (1992) [Nederlof II].

B. Patterson et al, "Detection of HIV–1 DNA and Messenger RNA in Individual Cells by PCR–Driven in situ Hybridization and Flow Cytometry", Science, 260:976–979 (May 14, 1993).

J. Prosser et al, "Sequence Relationships of Three Human Satellite DNAs", J. Mol. Biol., 187:145–155 (1986).

L. Sandell et al, "Loss of a Yeast Telomere: Arrest, Recovery, and Chromosome Loss", Cell, 75:729–739 (Nov. 19, 1993).

A. Therkelsen et al, "Staining of Human Telomeres with Primed in situ Labeling (PRINS)", Cytogenet Cell Genet, 68:115–118 (1995).

H. Vaziri et al, "Loss of Telomeric DNA During Aging of Normal and Trisomy 21 Human Lymphocytes", Am. J. Hum. Genet., 52:661–667 (1993) [Vaziri I].

H. Vaziri et al, "Evidence for a Mitotic Clock in Human Hematopoietic Stem Cells: Loss of Telomeric DNA with Age", Proc. Natl. Acad. Sci. USA, 91:9857–9860 (Oct., 1994) [Vaziri II].

J. Waye et al, "Human beta Satellite DNA: Genomic Organization and Sequence Definition of a Class of Highly Repetitive Tandem DNA", Proc. Natl. Acad. Sci. USA, 86:6250–6254 (Aug., 1989).

H. Willard et al, "Hierarchical Order in Chromsome–Specific Human Alpha Satellite DNA", TIG, 3(7):192–198 (Jul., 1987).

W. Wright et al, "Telomere Positional Effects and the Regulation of Cellular Senescence", TIG, 8(6):193–197 (Jun., 1992).

* cited by examiner

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:

```
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

CCCTAACCCT AA                                                          12

(2) INFORMATION FOR SEQ ID NO:2:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

CCCTAACCCT AACCCTAA                                                    18

(2) INFORMATION FOR SEQ ID NO:3:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

TTAGGGTTAG GG                                                          12

(2) INFORMATION FOR SEQ ID NO:4:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

TTAGGGTTAG GGTTAGGG                                                    18

(2) INFORMATION FOR SEQ ID NO:5:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

CCATTCCATT CCATT                                                       15

(2) INFORMATION FOR SEQ ID NO:6:

(i) SEQUENCE CHARACTERISTICS:
        (A) LENGTH: 14 base pairs
        (B) TYPE: nucleic acid
        (C) STRANDEDNESS: single
        (D) TOPOLOGY: linear
```

(ii) MOLECULE TYPE: DNA (genomic)

(xi) SEQUENCE DESCRIPTION: SEQ ID NO:6:

CCCATAACTA AACA                                                                    14

(2) INFORMATION FOR SEQ ID NO:7:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:7:

GAGAATTGAA CCACCG                                                                  16

(2) INFORMATION FOR SEQ ID NO:8:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:8:

TTCCCTGCCG TTCG                                                                    14

(2) INFORMATION FOR SEQ ID NO:9:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:9:

AATGGAATGG AATGG                                                                   15

(2) INFORMATION FOR SEQ ID NO:10:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:10:

TGTTTAGTTA TGGG                                                                    14

(2) INFORMATION FOR SEQ ID NO:11:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:11:

```
                                  -continued

CGGTGGTTCA ATTCTC                                                      16

(2) INFORMATION FOR SEQ ID NO:12:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

AAGGGACGGC AAGC                                                        14

(2) INFORMATION FOR SEQ ID NO:13:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

GGCGGCGGCG GCGGC                                                       15

(2) INFORMATION FOR SEQ ID NO:14:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

TCGTCGTCGT CGTCG                                                       15
```

METHOD FOR DETECTING MULTIPLE COPIES OF A REPEAT SEQUENCE IN A NUCLEIC ACID MOLECULE

This application claims the benefit of earlier filed Provisional Application No. 60/005,590, filed Oct. 12, 1995 and Provisional Application No. 60/007,616, filed Nov. 28, 1995.

FIELD OF THE INVENTION

The present invention relates to methods for detecting and optionally quantitating multiple copies of a repeat sequence in a nucleic acid molecule, preferably a telomere or centromere repeat sequence. The invention also relates to a method for determining the replicative potential of a cell.

BACKGROUND OF THE INVENTION

A large fraction of the DNA of all eukaryotes is made up of repeat sequences ranging from a few copies up to millions. Repeat functional sequences occur at the telomeres and centromeres of eukaryotic chromosomes. Telomeres and centromeres are important structural and functional elements of eukaryotic chromosomes. Telomeres are specialized nucleoprotein structures which are at the end of eukaryotic chromosomes (Blackburn, E H., Nature (London), 350:569–572, 1991). Telomeres in all vertebrates terminate in tandem arrays of the repeat sequence TTAGGG (Moyzis, R K., et al., Proc, Natl. Acad. Sci. USA 85:6622–6626, 1988). The repeat sequences are synthesized by the ribonucleoprotein enzyme telomerase, which is composed of both RNA and protein (Greider, C. W., & Blackburn, E. H. Cell 43:405–413, 1985; Morin, G B, Cell 59:521–529, 1989). In the absence of telomerase, telomeres shorten with cell divisions.

Telomeres have been shown to be critical for chromosome stability and function (Blackburn, E H., Nature (London), 350:569–572, 1991). Telomere loss has been shown to signal cell cycle arrest and chromosomal instability in yeast (Sandell, Ll, & Zakian, V A., Cell 57:633–643, 1989; and Greider, C. W., & Blackburn, E. H. Cell 43:405–413, 1985). Telomeres in cells have been found to shorten with the age of the cell donor (Allsopp, R C. et al., Proc. Natl. Acad. Sci. USA 89, 10114–10118, 1992; Lindsey, J. et al., Mutat. Tes. 256:45–48, 1991, Vaziri, H., et al., Am. J. Hum. Genet. 52:661–667, 1993, Vaziri, H., et al., Proc. Natl. Acad. Sci. USA 91:9857–9861, 1994, and Hastie, N D., et al., Nature (London)., 346:866–868, 1990), Harley C B et al., Nature (London) 345:458–460, 1990; Harley, C B, Mutat. Res. 256:271–282, 1991), and this phenomenon has been implicated by some in aging (Harley, C B, Mutat. Res. 256:271–282, 1991), and in programmed cell death (Wright et al., Trends Genet 8:193–197, 1992). Abnormalities in telomeres have also been found in malignant cells (Meltzer et al., Nature Genetics 4:252–255, 1993).

The centromere region of mammalian chromosomes consists of tandem arrays of repetitive sequences which consist of various copy numbers of $\alpha$ satellite (Willard, H F, Trends Genet. 3:192–198, 1987), $\beta$ satellite (Waye, J S., & Willard H F., Proc. Natl. Acad. Sci. USA 86:6250–6254, 1989) and the three classic satellites I, II and III (Prosser J. et al., J. Mol. Biol. 187:145–155, 1989).

Fluorescent in situ hybridization (FISH) techniques have been used to obtain information about the presence of telomeric and centromeric repeat sequences in chromosome preparations. Meyne and Moyzis (in Methods in Molecular Biology, Vol. 33: In Situ Hybridization Protocols, ed. K. H. A. Choo, 1994, Humana Press Inc., Totowa, N.J. USA) used FISH with synthetic oligonucleotide probes to confirm the presence of repeat telomere and centromere sequences. Directly labeled oligonucleotides should be attractive probes for FISH because of their small size (good penetration properties), single strand nature (no renaturation of probe required), and reproducible, controlled synthesis. However, these probes are not widely used for FISH because of their limited hybridization efficiency. The hybridization efficiency of oligonucleotide probes is modest because of their small size, and because conditions required for hybridization of the probe typically also favour the renaturation of denatured target DNA sequences with the longer homologous complimentary strands, resulting in direct and unfavourable competition for the oligo probe. Oligomer probes also have limited use as probes for single copy sequences.

Significantly, the studies using FISH have not provided optimal visualization of telomeres in a chromosome preparation nor have they provided information about the length of telomere or centromere regions. Southern analysis of the terminal restriction fragment (TRF) length distribution has so far been the only tool for studying telomere length (Allshire R C et al., Nucl. Acid Res. 17:4611–4627 and Harley C B et al., Nature 345:458–60). However, Southern analysis has a number of technical limitations. The TRF's contain DNA other than the telomeric repeat sequences such as degenerate or non-TTAGGG as well as TTAGGG repeats in blocks other than at the distal end (Allshire et al., Nucl. Acid Res. 17:4611–4627; Counter et al., EMBO J. 11:1921–9, 1992 and Levy et al., J. Mol. Biol. 225:951–960, 1992). There is also interchromosomal variation in both non-TTAGGG and TTAGGG DNA in the TRF and variation in prior replicative histories in vitro or in vivo of cells in the population of cells required for TRF analysis, which makes it difficult to assess the relationship between cell senescence and TRF length in specific chromosome's and in specific cell types. This is a particular problem in cancer where a variable or unknown number of normal cells may be present in a tumor sample.

It is apparent from the above discussion that there is a need for reliable methods for in situ visualization and quantification of telomere and centromere regions in chromosome preparations.

SUMMARY OF THE INVENTION

The present inventor has developed a method for detecting repeat sequences in the genome of a single cell or in an individual chromosome. This has been illustrated by the detection of telomeric repeat sequences at the end of human chromosomes. It was significantly found that the illustrated method results in the highly sensitive and efficient staining of all telomeres in a chromosome preparation. The present inventor also found a high correlation between fluorescence intensity of telomere sister chromatids in metaphase chromosomes. The method thus allows for the highly sensitive and efficient detection of telomeres in a chromosome preparation, and/or it allows for the quantification of the length of telomeric arrays at individual ends. The method also permits one skilled in the art to determine the effect of telomere loss on cell viability and chromosome behaviour in a variety of disease states.

The method of the invention can also be used to detect and/or quantitate the length of other repeat sequences for example, centromere repeats and polymorphisms of the telomere and centromere repeats.

The method of the invention addresses many of the technical limitations of conventional in situ hybridization procedures. The limitations of using oligonucleotide probes in in situ hybridization has been overcome by using nucleic acid analogue probes, and conditions that allow hybridization of the probes but prevent the renaturation of target DNA. The method of the invention provides a more efficient and sensitive procedure than existing or conventional in situ hybridization methods using DNA or RNA oligo probes.

Therefore, broadly stated the present invention relates to a method for detecting multiple copies of a repeat sequence in a nucleic acid molecule comprising (a) treating the nucleic acid molecule with a probe which is a nucleic acid analogue which is capable of hybridizing to the repeat sequence in the nucleic acid molecule and which is labelled with a detectable substance, under conditions permitting the probe to hybridize to repeat sequences in the nucleic acid molecule; and, (b) identifying probe hybridized to complementary repeat sequences in the nucleic acid molecule by directly or indirectly detecting the detectable substance.

In an embodiment of the invention, the detectable substance is a fluorophore, an image is formed of the probe hybridized to repeat sequences in the nucleic acid molecule, and, the multiple copies of the repeat sequences in the nucleic acid molecule are detected in the image.

The method of the invention may be used to quantitate the length of multiple copies of a repeat sequence in a nucleic acid molecule based on the direct relationship between the intensity of the signal produced directly or indirectly by the detectable substance, and the length of the multiple copies of the telomere sequence. Therefore, in accordance with a specific embodiment, the invention provides a method for quantitating the length of multiple copies of a repeat sequence in a nucleic acid molecule comprising (a) treating the nucleic acid molecule with a probe which is a nucleic acid analogue which is capable of hybridizing to the repeat sequence in the nucleic acid molecule and which is labelled with a detectable substance, under conditions permitting the probe to hybridize to repeat sequences in the nucleic acid molecule; (b) identifying probe hybridized to repeat sequences in the nucleic acid molecule by detecting a signal produced directly or indirectly by the detectable substance; and, (c) optionally, quantitating the length of the multiple copies of the repeat sequences in the nucleic acid molecule based on the direct relationship between the intensity of the signal produced directly or indirectly by the detectable substance and the length of the multiple copies of the repeat sequence.

The repeat sequence which is detected and/or quantitated is preferably a telomere or centromere repeat sequence, most preferably a human telomeric repeat sequence. In a preferred embodiment, multiple copies of the telomere repeat sequence TTAGGG in a nucleic acid molecule are detected using a probe containing the sequence CCCTAA.

In a particularly preferred embodiment of the invention, a method is provided for quantitating the length of multiple copies of the telomere repeat sequence TTAGGG in a nucleic acid molecule comprising (a) treating the nucleic acid molecule with a probe in the presence of a blocking reagent and a denaturing agent, preferably formamide, most preferably 70% formamide, and permitting the probe to hybridize to TTAGGG telomere repeat sequences in the nucleic acid molecule, wherein the probe is a nucleic acid analogue comprising the sequence CCCTAA and the probe is labelled with a fluorophore, and, (b) forming an image of probe hybridized to TTAGGG telomere repeat sequences in the nucleic acid molecule; and, (c) quantitating the length of the TTAGGG telomere repeat sequences in the nucleic acid molecule based on the direct relationship between fluorescence intensity and the length of the multiple copies of the telomere sequence.

The present invention also relates to a method for determining the replicative potential of a cell by quantitating the length of multiple copies of a telomere repeat sequence TTAGGG in nucleic acid molecules in the cell comprising (a) treating the nucleic acid molecules with a probe, under conditions permitting the probe to hybridize to telomere repeat sequences in the nucleic acid molecules, wherein the probe is a nucleic-acid analogue comprising the sequence CCCTAA and the probe is labelled with a detectable substance; (b) identifying probe hybridized to TTAGGG repeat sequences in the nucleic acid molecules by detecting signals produced directly or indirectly by the detectable substance; (c) quantitating the length of the multiple copies of the TTAGGG telomere repeat sequence based on the direct relationship between the intensity of the signals produced directly or indirectly by the detectable substance and the length of the multiple copies of the telomere repeat sequence and (d) determining the replicative potential by comparing the quantitated length of the multiple copies of the telomere repeat sequence with the length of multiple copies of the telomere repeat sequence associated with cells having a known replicative potential.

The invention still further contemplates a method for distinguishing normal cells from abnormal cells (e.g. tumor cells) in a cell suspension comprising: (a) treating the cells in the cell suspension with a probe which is a nucleic acid analogue which is capable of hybridizing to a repeat sequence in nucleic acid molecules in the nuclei of the cells and which is labelled with a detectable substance, under conditions permitting the probe to hybridize to repeat sequences in the nucleic acid molecules; (b) identifying probe hybridized to repeat sequences in the nucleic acid molecules by detecting a signal produced directly or indirectly by the detectable substance; and, (c) determining whether the cells are normal cells or abnormal cells by comparing the signal with a signal associated with known normal cells or abnormal cells. Preferably, the repeat sequence which is quantitated is a telomere repeat sequence, and the probe comprises the sequence CCCTAA.

In preferred embodiments of the methods of the invention, the detectable substance is a fluorophore, a digital image is created and the length of the multiple copies of the repeat sequence in the nucleic acid molecule is quantitated from the specific fluorescence intensity calculated from photon counts at defined positions within the digital image.

The methods of the invention may also be used to determine the effect of a substance on telomerase activity. Accordingly, the invention provides a method for determining the effect of a substance on telomerase activity comprising (a) treating cells having telomerase activity with a probe which is a nucleic acid analogue comprising the sequence CCCTAA and which is labelled with a detectable substance, preferably a fluorophore, and with a substance suspected of affecting telomerase activity, under conditions permitting the probe to hybridize to TTAGGG telomere repeat sequences in nucleic acid molecules in the cells; (b) identifying probe hybridized to TTAGGG telomere repeat sequences in the nucleic acid molecule by directly or indirectly detecting the detectable substance; (c) quantitating the length of multiple copies of the TTAGGG telomere repeat sequence in the nucleic acid molecules based on the direct relationship between the intensity of the signal produced directly or indirectly by the detectable substance and the length of the multiple copies of the telomere repeat sequence, and (d) determining the effect of the substance by comparing the quantitated length of the multiple copies of the telomere repeat sequence with the length of multiple copies of the telomere repeat sequence quantitated for the preparation in the absence of the substance.

The method of the present invention may be adapted to detect and/or quantitate multiple copies of repeat sequences in nucleic acid molecules in individual cells in suspension. In particular, the invention provides a method for quantitating multiple copies of repeat sequences in nucleic acid molecules in cells in suspension comprising; (a) treating the cells with a probe which is a nucleic acid analogue which is capable of hybridizing to the repeat sequences in the nucleic acid molecules and which is labelled with a detectable substance, under conditions permitting the probe to hybridize to repeat sequences in the nucleic acid molecules; (b) subjecting the treated cells to flow cytometry or image cytometry to detect the detectable substance and produce a signal corresponding to the amount of probe hybridized to repeat sequences in the nucleic acid molecules; and (c) optionally, quantitating the length of the multiple copies of the repeat sequences in the nucleic acid molecules based on the relationship between the intensity of the signal and the length of the multiple copies of the repeat sequences. In an embodiment, the method is used to quantitate multiple copies of a telomere repeat sequence TTAGGG. Preferably, the detectable substance is detected using flow cytometry which has the advantage that thousands of nuclei can be measured per second, and multiple other cell parameters (such as DNA content) can be analyzed simultaneously. The method is particularly suited for analyzing normal and abnormal cells, including lymphocytes, from blood and bone marrow.

The invention also contemplates a method for distinguishing normal cells from abnormal cells (e.g. tumor cells) in a suspension containing normal cells and abnormal cells comprising: (a) treating the cells in the cell suspension with a probe which is a nucleic acid analogue which is capable of hybridizing to a repeat sequence in nucleic acid molecules in the nuclei of the cells and which is labelled with a detectable substance, under conditions permitting the probe to hybridize to repeat sequences in the nucleic acid molecules; (b) subjecting the treated cells to flow cytometry or image cytometry to detect the detectable substance and produce a signal corresponding to the amount of probe hybridized to repeat sequences in the nucleic acid molecules; and (c) determining whether the cells are normal cells or abnormal cells by comparing the signal with a signal obtained for known normal cells or abnormal cells.

The invention also contemplates novel Peptide Nucleic Acid (PNA) probes. In particular, the invention relates to a Peptide Nucleic Acid (PNA) probe comprising the following sequence: TTAGGG, CCCTAA, CCCCAA, CCCCAAAA, CCCACA, CCCTAAA, CCCCT, or CCATT. Preferred Peptide Nucleic Acid (PNA) probes of the invention include CCCTAACCCTAA [SEQ ID no: 1], CCCTAAC-CCTAAACCTAA [SEQ ID no: 2], TTAGGGTTAGGG [SEQ ID no: 3], TTAGGGTTAGGGTTAGGG [SEQ ID no: 4], CCATTCCATTCCATTCATT [SEQ ID no: 5], CCCAT-AACTAAACA [SEQ ID no: 6], GAGAATTGAACCACCG [SEQ ID no: 7], TTCCCTGCCGTTCG [SEQ ID no: 8], $(GGC)_5$ [SEQ ID no: 13], or $(TCG)_5$ [SEQ ID no: 14].

The invention also contemplates kits for performing the methods of the invention.

These and other aspects of the present invention will become evident upon reference to the following detailed description and attached drawings. In addition, reference is made herein to various publications, which are hereby incorporated by reference in their entirety.

BRIEF DESCRIPTION OF THE DRAWINGS

The invention will now be described with reference to the accompanying drawings, in which.

DETAILED DESCRIPTION OF THE INVENTION

Figure 1:
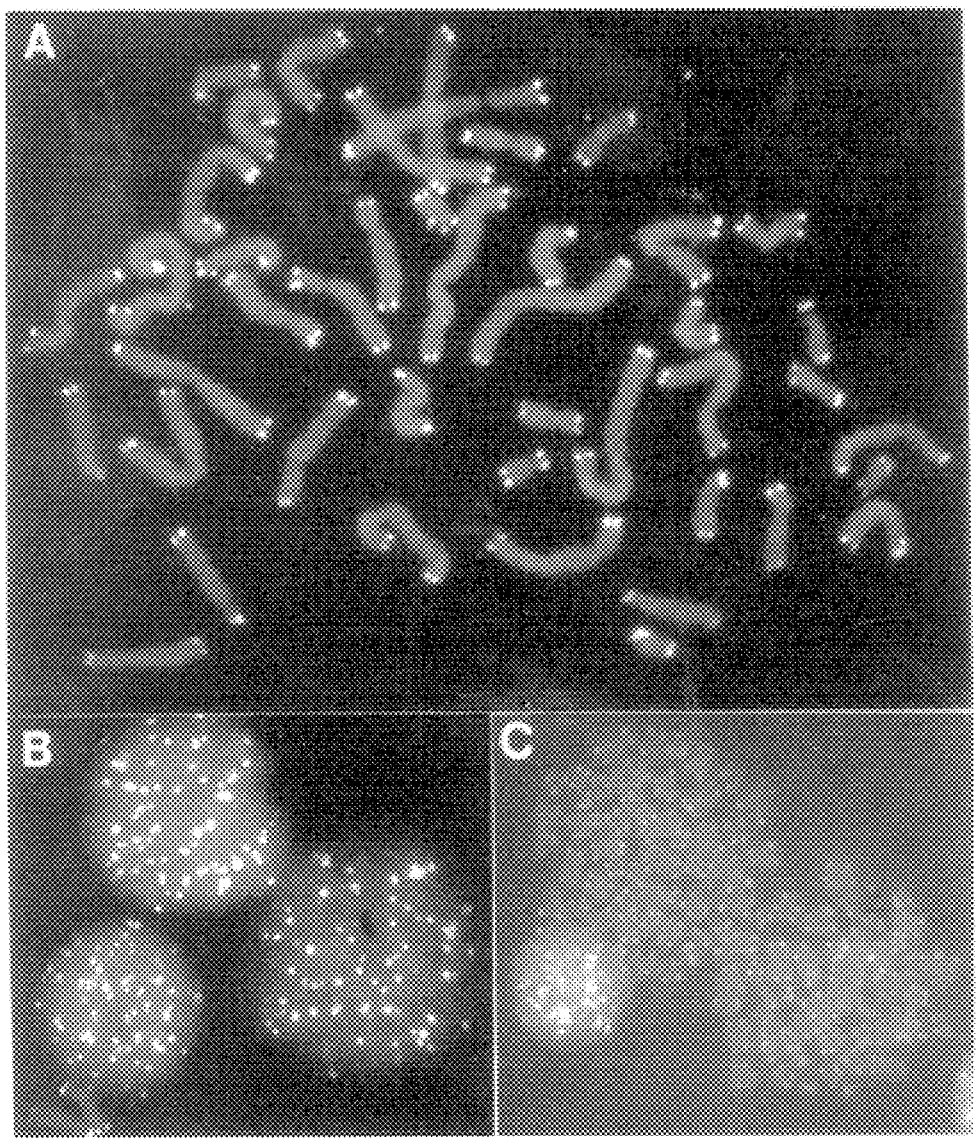
FIG. 1 shows images of in situ hybridization of telomeric nucleic analogue probes to metaphase chromosomes and interphase nuclei from cultured human fetal liver cells.

As hereinbefore mentioned, the present invention relates to a method for detecting and/or quantitating the length of multiple copies of a repeat sequence in a nucleic acid molecule comprising (a) treating the nucleic acid molecule with a probe which is a nucleic acid analogue which is capable of hybridizing to repeat sequences in the nucleic acid molecule, and which is labelled with a detectable substance, under conditions permitting the probe to hybridize to the repeat sequences in the nucleic acid molecule; (b) identifying probe hybridized to the repeat sequences in the nucleic acid molecule by detecting a signal produced directly or indirectly by the detectable substance; and (c) optionally quantitating the length of multiple copies of a repeat sequence in the nucleic acid molecule based on the direct relationship between the intensity of the signal produced directly or indirectly by the detectable substance and the length of the multiple copies of the repeat sequence.

The nucleic acid molecules that are analyzed using the methods of the invention are preferably double stranded DNA molecules. However, the methods of the invention may be adapted to quantitate single stranded DNA, and RNA molecules.

The nucleic acid molecules which are detected and/or quantitated using the methods of the invention contain repeat sequences which may be multiple copies of a single sequence, or regularly alternating combinations of several sequences. The repeat sequences may be "pure" with no other kinds of sequences inserted, or clusters interrupted at points by one or more repeats of a pseudogene, or other moderately repeated element. Examples of repeat sequences that may be analyzed using the methods of the invention are telomere repeat sequences (e.g. GGGATT, GGGATTT, GGGGA, GGGTGT, GGGGTTTT, GGGGTT), centromere repeat sequences (e.g. AATGGAATGGAATGG [SEQ ID no: 9], TGTTTAGTTATGGG [SEQ ID no: 10], CGGTG- GTTCAATTCTC [SEQ ID no: 11]), or the gene encoding 5S RNA (AAGGGACGGCAAGC [SEQ ID no: 12]). Trinucleotide simple tandem repeats may also be analyzed using the methods of the invention. For example, the trinucleotide simple tandem repeat CCG which gives rise to one group of fragile sites on human chromosomes which are responsible for the most common familial form of mental retardation; and the trinucleotide simple tandem repeat AGC which gives rise to a number of neurological disorders (Sutherland, G. R. and R. I. Richards, Proc. Natl. Acad. Sci. USA 92:3636, 1995) may be analyzed using the methods of the invention.

Nucleic acid molecules present in morphologically preserved chromosomes, cells and tissue sections may be analyzed using the methods of the invention. The nucleic acid molecules are typically from metaphase cells. Biological materials are morphologically preserved by fixation using conventional methods (See for example, A. G. Everson Pearce, Histochemistry Theoretical and Applied, 4th Ed., Churchill Livingstone, Edinburgh, 1980 for details relating to the general techniques of preparing tissue sections and fixation). They may be fixed on a support such as slides or filters using a fixative. By way of example, samples of hematopoietic cells may be fixed by spinning small volumes of cells onto slides. The preparations containing the nucleic acid molecules may also be pretreated on the support. Pretreatments include RNAse treatment to remove endogenous RNA, protease treatment (e.g. pepsin) to increase the accessibility by digesting protein surrounding the target nucleic acid molecules, and detergent treatment when it is suspected that lipid membrane components have not been extracted by other procedures.

In a preferred embodiment of the invention for detecting multiple copies of a telomeric repeat sequence in a nucleic acid molecule and optionally quantitating the length of the multiple copies of the telomeric repeat sequence, cells are cultured, treated with colcemid (e.g. 0.1 μg/ml), harvested about 2 to 18 hours later, and after washing hypotonic swelling cells are fixed and stored in methanol/acetic acid. Cells are fixed to slides by spinning small volumes (e.g. 10–100 μl) of cells in acetic acid, drying the cells overnight, and immersing in a buffer (e.g. PBS), prior to fixation in formaldehyde (e.g. 4%). The cells are then washed, treated with pepsin (e.g. 1 mg/ml) and rinsed with buffer. The formaldehyde fixation procedure is repeated and the slides are dehydrated in ethanol and dried.

In the methods of the invention employing image or flow cytometry, the nucleic acid molecules are present in cell suspensions. The cells are typically interphase cells. Generally, in the cytometry methods, cells are harvested, washed, and fixed with an agent such as PFX (Caltag Fixation and Permeabilization reagent) or PermeaFixt (Ortho #775999). The cells in the suspension may be pretreated with RNase and pepsin as described herein.

The preparations containing the nucleic acid molecules are treated with a probe. The probe is a nucleic acid analogue and it is capable of hybridizing to a repeat sequence. Nucleic acid analogues differ from natural DNA in that they do not have a deoxyribose or ribose backbone. Suitable probes for use in the present invention are those constructed from the nucleic acid analogue known as Peptide Nucleic Acid (PNA) which contains a polyamide backbone (See PCT WO 92/2070, which is incorporated herein in its entirety by reference), or analogues having cyclic backbone moieties comprising furan or morpholine rings, or acyclic backbone moieties as described in PCT WO 86/05518, which is incorporated herein in its entirety by reference. Preferably, the probe used in the methods of the invention is a PNA. Determination of whether a probe hybridizes to a repeat sequence can be accomplished by hybridizing the probe to a nucleic acid molecule containing multiple copies of the repeat sequence using the hybridization media and conditions described herein.

In an embodiment of the invention for detecting and optionally quantitating the length of telomere repeats in a nucleic acid molecule, the hybridization probe is a PNA containing the repeat sequence TTAGGG, CCCTAA, CCCCAA, CCCCAAAA, CCCACA, CCCTAAA, or CCCCT, most preferably CCCTAA. For example, a probe which may be used in the present invention is a PNA having the following sequence: CCCTAACCCTAA [SEQ ID no: 1], CCCTAACCCTAACCCTAA [SEQ ID no: 2], TTAGGGT-TAGGG [SEQ ID no: 3], or TTAGGGTTAGGGTTAGGG [SEQ ID no: 4].

In another embodiment of the invention for detecting and optionally quantitating the length of multiple copies of a centromere repeat sequence common to human satellites II and III in a nucleic acid molecule the hybridization probe is a PNA containing the repeat sequence CCATT, for example, CCATTCCATTCCATT [SEQ ID no: 5]. In other embodiments of the invention for detecting and optionally quantitating the length of multiple copies of a centromere repeat sequence specific for the centromeric region of the X chromosome, and for detecting and optionally quantitating the length of multiple copies of a centromere repeat sequence for specific chromosome 18 in a nucleic acid molecule, the hybridization probe is preferably a PNA having the sequence CCCATAACTAAACA [SEQ ID no: 6], and GAGAATTGAACCACCG [SEQ ID no: 7] respectively.

The method of the invention may also be used to detect and optionally quantitate the length of the 5S RNA gene, and the probe which is used in the method is preferably a PNA having the sequence TTCCCTGCCGTTCG [SEQ ID no: 8]. Further, the invention may be used to detect and/or quantitate the trinucleotide simple tandem repeat CCG and the trinucleotide simple tandem repeat AGC, using PNA probes for example having the following sequences: $(GGC)_5$ [SEQ ID no: 13], and $(CG)_5$ [SEQ ID no: 14].

The probe used in the method of the invention is preferably labelled with one or more detectable substances. In the direct methods contemplated by the present invention the probe is labelled with a detectable substance so that the formed hybrids can be visualized microscopically after the in situ hybridization procedure, or detected using flow cytometry or image cytometry. Detectable substances which may be used in direct methods include fluorophores, isotopes, and chemiluminescent compounds. Examples of suitable isotopes include iodine $I^{125}$, $I^{131}$ or tritium; examples of suitable fluorophores include fluoresceinisothiocyanate (FITC), tetramethyl rhodamine isothiocyanate (TRITC), amino-methyl coumarin acetic acid (AMCA) (Molecular Probes, Eugene, Oreg.), Texas Red (Molecular Probes, Eugene, Oreg.) and carboxylmethylindocyano dyes such as Cy2, Cy3, or Cy5 (Biological Detection Systems, Pittsburgh, Pa.), and, an example of a chemiluminescent material is luminol. The probe may be labelled with these detectable substances using methods conventionally known in the art.

In the indirect methods contemplated by the present invention the probe is labelled with a detectable substance so that the formed hybrids are visualized after reacting with an element (e.g. a substrate, antibody, etc.) which results in a detectable signal. Detectable substances which may be used in indirect methods include enzymes and haptens. Examples of suitable enzymes include horseradish peroxidase, alkaline phosphatase, β-galactosidase, or acetylcholinesterase; and examples of suitable haptens include biotin and digoxigenin. By way of example, when biotin is used as the detectable substance, in situ hybridized sequences are identified using (strept)avidin or anti-biotin antibodies. The probe may be labelled with enzymes and haptens using methods conventionally known in the art (see for example, Patterson et al., Science 260:976–979, 1993).

It will be appreciated that a probe used in a method of the invention may be labelled with more than one detectable substance. For example, one probe may be labelled with two or more fluorophores. It will be appreciated that the probe may be labelled with detectable substances for both direct and indirect methods. For example, a probe may be labelled with both a fluorophore and an enzyme or hapten The method of the invention may also use differently labelled probes. For example, the method may use three probes having the same nucleic acid sequence but each labelled with a different detectable substance, for example, three different fluorophores.

The detectable substance(s) may provide a colorimetric, photometric, radiometric etc. signal which can be detected by a wide variety of means. For example, the method of the invention could employ a suitable detection device capable of detecting a change in absorption density, a change in fluorescent, or radioactive emission, or a shift in the absorbance of a characteristic $\lambda$ max.

In a preferred embodiment of the invention the probe is labelled with a fluorophore such as fluorescein-isothiocyanate (FITC), tetramethyl rhodamine isothiocyanate (TRITC), amino-methyl coumarin acetic acid (AMCA) (Molecular Probes, Eugene, Oreg.), Texas Red (Molecular Probes, Eugene, Oreg.), or carboxylmethylindocyano dyes such as Cy2, Cy3, or Cy5 (Biological Detection Systems, Pittsburgh, Pa.), and images of fluorophore labelled probes hybridized to target repeat sequences in the nucleic acid molecule are created using conventional techniques known in the art (See for example, Nederlof P M et al., Cytometry 13:839–845, 1992 which is incorporated herein in its entirety by reference). Preferably, the images are formed electronically, most preferably digital images are formed.

Generally, the instrumentation needed to create a digital image consists of a microscope system, a detector for collection of images, and computer hardware and software for image storage and analysis. For fluorescence microscopy objective lenses are generally used with high magnification and high numerical aperture, since these characteristics determine the spatial resolution and light collecting properties. By way of example, a Leits Dialux epifluorescence microscope equipped with a 100 W mercury-arc lamp and a Neofluor 1,40 NA oil objective may be used to measure fluorescence, and the filter used for the selection of the fluorophore may be as follows: PL450-SP490 (excitation filter), DM510 (dichroic mirror), and LP515-SP560 (emission filters).

A detector for imaging the FISH results should be selected so that it has sufficient sensitivity to detect the fluorescing signals obtained by FISH. Ideally the detector also provides a linear response to a wide range of wavelengths, has a high signal to noise ratio, and has wide dynamic range and little geometric aberrations. The cooled CCD camera generally fulfils these requirements (Aikens R S et al., Methods Cell Biol. 29:291, 1989, Hiraoka et al., Science 238:36–41, 1987, Photometrics, Tucson, Ariz.), with a Kodak chip with 1,024×1,345 elements of 6.8×6.8 $\mu$m each.

The image collection and image analysis may be performed as described in Smith, L. C. et al, (Methods Enzymol. 129:857–873, 1986). The intensity of a spot may be calculated as the integrated intensity of all pixels within the area of the spot corrected for the (local) background. The local background may be determined by the minimum-maximum digital filtering technique (Verbeek P. W. et al., Signal Processing 15.249–258, 1988).

In embodiments of the invention where a digital image is formed, the length of the multiple copies of the repeat sequence in the nucleic acid molecule is quantitated from the specific fluorescence intensity calculated from photon counts at defined positions within the digital image as described in detail in Example 1.

Methods of the invention are contemplated herein which employ flow cytometry or image cytometry. In such methods, the cells pass through detectors, and the signals generated by the detectable substance are resolved and detected using instruments such as confocal microscopes or optical sectioning fluorescence microscopes. A flow histogram is obtained which shows signals corresponding to the intensity of the detectable substance. The relative length of multiple copies of a repeat sequence are determined based on the intensity of the signal. Suitable detectors and instruments which may be used to carry out flow cytometry and image cytometry are commercially available, for example, the FACScan (Becton Dickinson, San Jose, Calif.) flow cytometer, and the DeltaVision optical sectioning fluorescence microscope from Applied Precision (Mercer Island, Wash.).

The concentration of probe used in the methods described herein may be selected by titrating increasing amounts of the probe and determining the concentrations which provide plateau hybridization. These concentrations are preferably used in the method of the invention. In a preferred embodiment of the invention for visualizing and optionally determining the length of telomere repeats in nucleic acid molecules in morphologically preserved materials, the amount of hybridization probe used is between 0.1–10 $\mu$g/ml, preferably 0.3 $\mu$g/ml.

The hybridization probe is incorporated into a hybridization medium. The hybridization medium and hybridization conditions are selected so as to favour hybridization of the probe with the denatured nucleic acid molecules in the preparation to be tested, and disfavour renaturation of the denatured nucleic acid molecules with their complementary single strand.

Generally, a hybridization medium is selected which has a low ionic strength and typically contains a buffer, denaturing agent and blocking reagent. Suitable buffers include TRIS and Hepes. Examples of suitable denaturing agents are formamide and DMSO. A blocking reagent is selected so that it substantially blocks non-specific binding of the probe. Examples of blocking reagents which may be used in the method of the invention are protein solutions such as BMP (Boehringer-Mannheim, Gmbh, FRG).

In a preferred embodiment of the method of the invention for detecting and/or determining the length of multiple copies of a telomeric repeat in a nucleic acid molecule, the hybridization medium contains a buffer (e.g. 10 mM TRIS, pH=7.2), formamide 50% –100%, most preferably 70% formamide, BMP (1–5% W/V, most preferably 1% W/V), and the labelled probe.

The hybridization medium containing the hybridization probe may be applied to the morphologically preserved biological materials. Generally, 5 to 20 $\mu$l, preferably 10 $\mu$l of the hybridization medium is applied per cell preparation. The hybridization probe is applied and the target nucleic acid molecules are denatured simultaneously by heat or pH treatment, preferably the mixture is treated for 0.1 to 24 hours at 70 to 80° C., most preferably 3 minutes at 80° C. Hybridization is carried out for about 0.1 to 24 hours, most preferably 2 hours, at 4 to 40° C., preferably 25° C. After hybridization, the slides are washed with a buffer (e.g. TWEEN™ and/or Tris buffer).

In the methods of the invention for detecting and/or quantitating multiple copies of a repeat sequence in cell suspensions, about 10 to 1000 μl, preferably 200 μl of hybridization medium is added to the cells. The hybridization is carried out for about 5 min to 24 hours, preferably 8 to 18 hours at room temperature. After hybridization the cells are washed with buffer (e.g. formamide/BSA/TWEEN™; Tris/NaCl/Tween/BSA) and resuspended in buffer (e.g. PBS and 7AAD for FACSort; DAPI for FACStar).

The method of the present invention in providing a means to detect and/or quantitate the length of repeat sequences in nucleic acid molecules has many practical applications. The efficient and sensitive hybridization in the method of the invention permits the detection of repetitive sequences in many cytogenic analyses. In particular, the method provides more reliable detection of chromosomal abnormalities than conventional methods. Furthermore, since nearly 25% of the human genome consists of repetitive sequences, data on the distribution of these sequences, and in particular quantitative data, will permit highly specific aneuploidy enumeration and detection, as well as enumeration and detection of telomere abnormalities.

The quantification of the length of telomeric arrays at individual ends of chromosomes using the methods of the invention permits one skilled in the art to determine the effect of telomere length on cell viability and chromosome behaviour. In particular, the methods of the invention may be used to analyze pathophysiology of telomere length dynamics in cells from normal and abnormal tissues.

The methods described herein may be used to obtain quantitative information on the relationship between telomere length and disease which will guide the development of novel therapeutic strategies involving for example transplantation and genetic manipulation of primitive hematopoietic cells for the treatment of a variety of disorders.

The methods of the invention may also be used to assess the replicative potential of a cell. The term "replicative potential" refers to the ability of a cell to divide, or the number of times a cell can turnover. Replicative potential may be directly linked to the length of telomeres, and the latter provide an indication of the age of a cell. Therefore, the present invention also provides a method for determining the replicative potential of a cell which involves quantitating telomere length using the method described above and illustrated in the examples. In particular, the method comprises (a) treating nucleic acid molecules in cells with a probe which is a nucleic acid analogue comprising the telomere repeat sequence CCCTAA, which is labelled with a detectable substance, under conditions such that the nucleic acid molecules are denatured and the probe hybridizes to telomere repeat sequences in the nucleic acid molecules; (b) identifying probe hybridized to TTAGGG telomere repeat sequences in the nucleic acid molecule by detecting signals produced directly or indirectly by the detectable substance; (c) quantitating the length of the multiple copies of the telomere repeat sequence based on the direct relationship between the intensity of the signal produced directly or indirectly by the detectable substance and the length of the multiple copies of the telomere sequence; and (d) determining the replicative potential by comparing the quantitated length of the multiple copies of the telomere repeat sequence with the length of multiple copies of the telomere repeat sequence associated with cells having a known replicative potential (e.g. normal cells, disease cells). The preparation of a sample containing nucleic acid molecules, and the hybridization, denaturation and imaging steps may be carried out as described herein.

The method for determining the replicative potential of a cell can be used to monitor the progression of disease. The advanced stages of some diseases (e.g. some cancers) are characterized by aberrant cells with short telomeres and an indefinite replicative potential. Generally, primary and metastatic human tumors have extremely short telomeres, express the enzyme telomerase, and thus express a high replicative potential. The average length of the TTAGGG repeat arrays has been estimated to be about 1 to 2 kb per chromosome end. Therefore, the quantification of telomeres in tumor cells from a patient may suggest that the tumor is a primary or metastatic tumor, and guide development of drugs capable of inhibiting telomerase activity.

The determination of replicative potential may be particularly useful in monitoring the progression of leukemia. In the initial stages of leukemia, altered signal transduction pathways and/or altered probabilities of differentiation events in a single cell will result in numerical expansion of the leukemic cells. This expansion is eventually limited by critical shortening of telomeric DNA, resulting in signals that trigger cell cycle arrest but also chromosomal instability. Further progression of the disease may involve selection of cells that ignore or can bypass the cell cycle arrest signal and eventually selection of cells that express the enzyme telomerase.

In some diseases the replicative potential of aberrant cells or infected cells declines with the progression of the disease. For example, the replicative potential of lymphocytes declines over time after infection with the Human Immunodeficiency Virus (HIV). Therefore, the progression of an HIV infection may be monitored by determining the replicative potential i.e. telomere length in nucleic acid molecules from specific lymphocyte subpopulations from a patient infected with HIV.

It may also be possible to extend or maintain the proliferative potential of cells for example, adult stem cells by forced expression of exogenous or endogenous telomerase activity. The method of the present invention may be used to monitor telomere length and determine telomerase activity which provides optimal proliferation of the cells.

The methods of the invention may be used for the diagnostic analysis of tissue sections to distinguish cells with different proliferative histories. For example, tumor cells that by morphology alone are often difficult to distinguish from neighboring normal cells can be distinguished from normal cells by a weaker "telomere-staining" in their nucleus following the methods of the invention. Because telomere shortening in tumor cells is a parameter that is independent from commonly used morphological parameters, quantitative information on telomere fluorescence per nucleus is an extremely valuable aid in the diagnosis or analysis of tissue sections of patient material.

The present invention provides a method of measuring telomere repeat content in individual cells by flow cytometry. Currently no methods exist to assess the replicative history (and implicated replicative potential) of cells by flow cytometry. However, such a method would permit identification of abnormal cells in a variety of disorders. Cells that, by morphology alone appear normal, could, for the first time, be identified as being abnormal in telomere content, and therefore cell divisional history, relative to other cells from the same individual. This type of analysis is particularly useful in the analysis of blood cells. For example, the presence of morphologically "normal" lymphocytes could raise the suspicion of a pathologist if such cells by telomere-PNA-FISH flow cytometry analysis stained significantly weaker than other cells from the same patient. Such cells could be sorted and analyzed for the presence of tumor-specific genetic abnormalities of, for example, lymphoma cells. Measurements of telomere repeat content in different subpopulations of lymphocytes could provide useful information about the immune status of an individual. For example, the functional properties of lymphocytes with a low telomere repeat content, as measured using the method of the invention using flow cytometry, may be compromised. Identification of such cells may therefore be of prognostic significance in that the presence of such cells may predict the onset of specific immune defects. An example of such a use of such a method is the identification of specific lymphocyte subpopulations (i.e. cells expressing CD4 or CD8) in patients infected with the HIV virus that are at a high risk for developing AIDS. Similar assessment of telomere content in antigen-specific subpopulations may provide information on the immune status of individuals that cannot be obtained otherwise.

The methods described herein may also be used to determine the effect of a substance on telomerase activity. Accordingly, the invention provides a method for determining the effect of a substance on telomerase activity comprising (a) treating cells having telomerase activity with a probe which is a nucleic acid analogue comprising a telomere repeat sequence containing the sequence CCCTAA and which is labelled with a detectable substance, and with a substance suspected of affecting telomerase activity, under conditions such that the probe hybridizes to TTAGGG telomere repeat sequences in nucleic acid molecules in the cells; (b) identifying probe hybridized to complementary telomere repeat sequences in the nucleic acid molecules by detecting a signal produced directly or indirectly by the detectable substance; (c) quantitating the length of the multiple copies of the telomere repeat sequence based on the direct relationship between the intensity of the signal produced by the detectable substance and the length of the multiple copies of the telomere sequence and (d) determining the effect of the substance by comparing the quantitated length of the multiple copies of the telomere repeat sequence with the length of multiple copies of the telomere repeat sequence quantitated for the preparation in the absence of the substance.

Cells having telomerase activity which may be used in the above-described method include cells in adult male germline tissues such as testes, cells from malignant or metastatic tumors such as breast, ovarian, prostate, CNS, head and neck, colon, uterine cancer, and hematopoietic cells from late stage chronic lymphocytic leukemia (CLL).

Substances identified using the present invention may be used as inhibitors or stimulators of telomerase activity. Inhibitors of telomerase identified using the method described herein may be useful as anti-cancer therapeutics. Substances which stimulate telomerase activity may be useful in the treatment of conditions where the replicative potential of cells declines over time such as after infection with HIV.

The reagents suitable for applying the methods of the invention to detect multiple copies of repeat sequences, preferably, telomere repeat sequences, may be packaged into convenient kits providing the necessary materials packaged into suitable containers. For example, such kits may include the necessary probes, reagents, and buffers, and instructions for in situ hybridization by means of the methods described herein. The kits may also include suitable supports useful in performing the methods of the invention.

The following non-limiting examples are illustrative of the present invention:

EXAMPLES

Example 1

The following materials and methods were used in the studies set out in the example:

Hybridization Protocol

Cultures of hematopoietic cells from human fetal liver, umbilical cord blood and adult bone marrow were prepared as described in Hastie, N. D. et al., Nature 346:866, 1990. At various time intervals colcemid (0.1 µg/ml) was added to the cultures and cells were harvested 2 to 18 hours later. After washing and hypotonic swelling, cells were fixed and stored in methanol/acetic acid fixative using standard procedures. Cells were fixed to slides by spinning small volumes (10–100 µl) of cells in 2 ml of 50% acetic acid. The slides were dried overnight in air and immersed in Phosphate Buffered Saline (PBS) for 5 min. prior to fixation in 4% formaldehyde in PBS for 2 minutes, washed in PBS (3×5 min.) and treated with pepsin (P-7000, Sigma, St. Louis, Mo.) at 1 mg/ml for 10 min. at 37° C. at pH 2.0. After a brief rinse in PBS, the formaldehyde fixation and washes were repeated and the slides were dehydrated in ethanol and air dried. Ten microliters of hybridization mixture containing 70% formamide, 0.3 µg/ml FITC-$(C_3TA_2)_3$ PNA probe (PBIO/Biosearch Product, Bedford, Mass.), 1% (W/V) blocking reagent (Boehringer-Mannheim, Gmbh, FRG) in 10 mM Tris pH 7.2 was added to the slide, a coverslip (20×20 mm) was added and DNA was denatured by heat for 3 min. at 80° C. After hybridization for 2 hours at room temperature, the slides were washed with 70% formamide in 10 mM Tris pH 7.2 (2×15 min.) and with 0.05 M tris 0.15 M NaCl pH 7.5 containing 0.05% Tween-20 (3×5 min.). The slides were then dehydrated with ethanol, air dried and covered by 5–10 µl of antifade solution (VectaShield, Vector Laboratories Inc., Burlingame, Calif.) containing 0.1 µg/ml of propidium iodide.

Image Collection and Analysis

Digital images were recorded with a KAF 1400 slow scan CCD camera (Photometrics; Tuscon, Ariz.) on an Aristoplan fluorescence microscope (Leica, Wetzlar, Germany), interfaced to a Sun 330 Workstation. Microscope control and image analysis was performed under "SCIL Image" (TN), Delft; Netherlands). A PL Fluotar 100×NA 1.3 objective lens and filter blocks 13 and N2.1 were used for the visualization of FITC and Propidium, respectively. A short pass SP 560 nm filter was inserted at the emission side when the green FITC emission was recorded, to minimize crosstalk of red propidium signal into this channel. The camera housing contained a short pass SP 630 nm filter to block the far red and infra red light during all measurements. Integration times were chosen such that approximately 50% of the dynamic range of the camera was used (typically 9 sec for the FITC telomere signal and 6 sec for the Propidium counter stain). Digital images of 12 bit were corrected for pixel shifts (occurring due to the change of optical filters) by software procedures as described in Nederlof, P. M. et al., Cytometry 13:846, 1992. A second correction procedure was performed to subtract the dark current image and to correct for uneven illumination of the microscopic field and local differences in sensitivity of the camera, using constantly fluorescing uranyl glass as a reference object. Thus recorded and corrected images were segmented on the basis of grey value thresholding to find the contours of the chromosomes and the telomeric regions. For each of the telomeric regions, a background subtraction was performed based on min/max filtering. Each chromosome was divided in four regions by a watershed algorithm, and the integrated fluorescence intensity of each telomeric region was calculated and divided by the integration time used for normalization purposes. Finally, for each chromosome the spot intensities were ordered two by two and summarized.

Results

In initial studies, FITC-labeled DNA, RNA and PNA $(C_3TA_2)_3$ oligonucleotide probes were directly compared for the detection of $T_2AG_3$ repeats on human metaphase chromosomes by in situ hybridization. At selected hybridization conditions (Meyne, J., and Moyzis, R. K., Methods Mol. Biol. 33:63, 1994) all three probes showed fluorescence of some telomeres. Hybridization with the RNA probe appeared somewhat more efficient than with the DNA oligo but neither of these two probes allowed staining of all telomeres in agreement with previous findings by others (Moyzis, R. K. et al, Proc. Natl. Acad. Sci. U.S.A. 85: 6622, 1988, Meyne, J. and Moyzis, R. K., Methods Mol. Biol. 33:63. 1994). The PNA probe showed a high background fluorescence but also intense staining of most telomeres. Further optimization of the hybridization protocol for use with the PNA probe (see above) resulted in microscopic images exemplified in FIGS. 1 and 2.

In particular, FIG. 1 shows in situ hybridization of peptide nucleic acid probe to metaphase chromosomes and interphase nuclei from cultured human fetal liver cells. Hybridization of the FITC-labeled $(C_3TA_2)_3$ PNA probe at room temperature for 2 hours was performed at low ionic strength 10 mM Tris/70% formamide in the presence of excess protein as described herein. Chromosomes were counter-stained with propidium iodide (orange, A&B) or diamidinophenylindole (DAPI, Blue, C). Photographs were taken directly from the microscope using a 100× objective. Note that in FIG. 1 essentially all metaphase chromosomes show four fluorescent spots and that the fluorescence intensity of sister chromatid telomere pairs appears to be linked. Specific fluorescence was completely inhibited by including a 3-fold molar excess of an unlabeled $(T_2AG_3)_2$ peptide nucleic acid oligonucleotide but not a 100-fold molar excess or random nucleotide peptide oligomer in the hybridization mixture.

Figure 2:
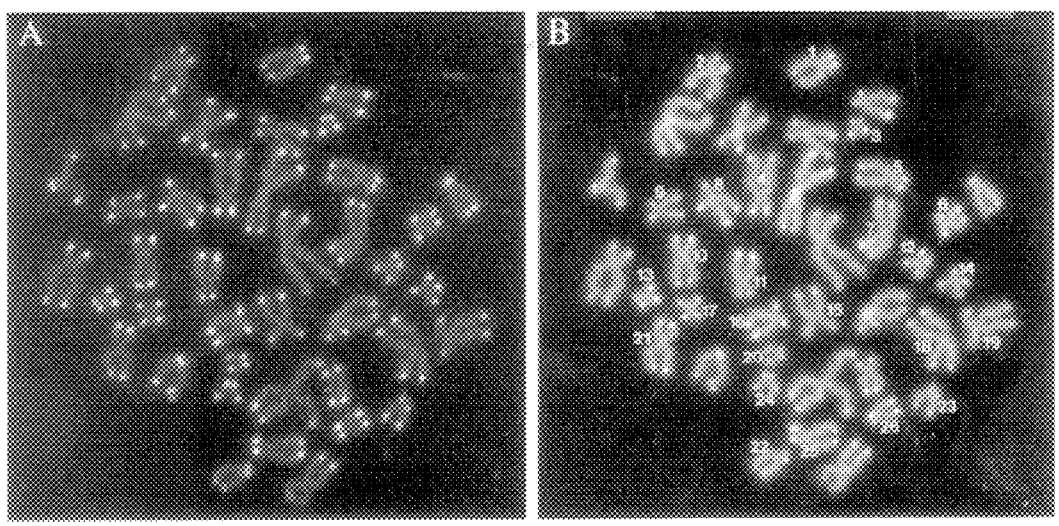
FIG. 2 shows examples of digital images of in situ hybridization of FITC-$(C_3TA_2)_3$ PNA probe to metaphase chromosomes used for calculations of fluorescence intensity of individual telomeres.

FIG. 2 shows an example of the digital images of in situ hybridization of FITC-$(C_3TA_2)_3$ PNA probe to human fetal liver metaphase chromosomes used for calculations of fluorescence intensity of individual telomeres. Microscopic images were captured with a cooled CCD camera (Photometrics) using blue excitation and filters for separate collection of green fluorescence (FITC) and green plus red fluorescence (mainly Propidium iodide). The image of total fluorescence (B) was used to identify chromosomes and areas in (A) for calculations of specific hybridization signals on individual telomeres (see description of image collection and analysis above).

Figure 3:
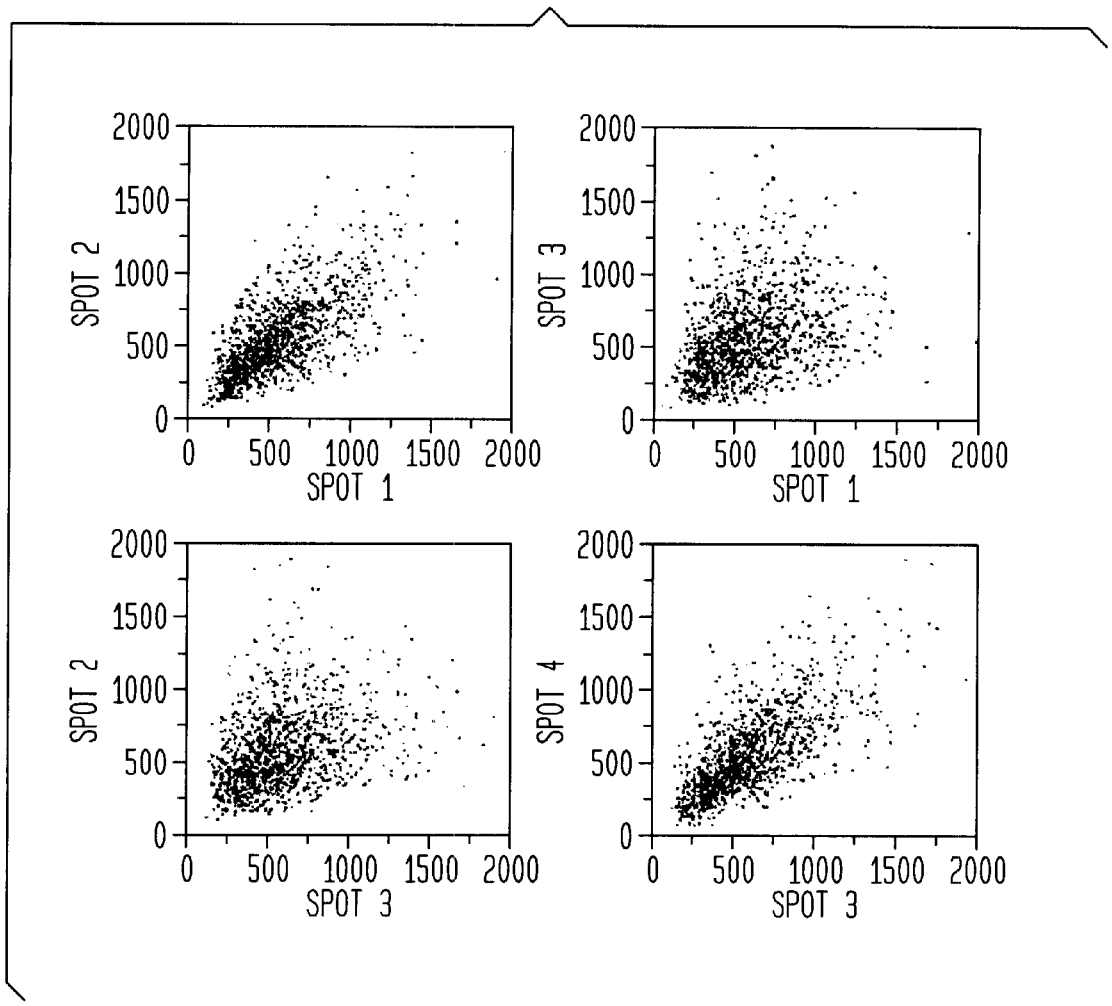
FIG. 3 are graphs showing correlation of telomere fluorescence of sister chromosomes in metaphase chromosomes.

Essentially all metaphase chromosomes showed four fluorescent spots at telomeric positions (FIGS. 1A and 1C) and up to 92 spots were observed in interphase nuclei (FIG. 1B). This was an unexpected result, given the limitations in the efficiency of regular oligonucleotide hybridization (Moyzis, R. K. et al, Proc. Natl. Acad. Sci. U.S.A. 85: 6622, 1988, Meyne, J. and Moyzis, R. K., Methods Mol. Biol. 33:63. 1994) or the more sensitive primed in situ hybridization (A. J. Therkelsen, et al., Cell Genet. 68:115, 1995) for detection of telomeric repeats. Furthermore, the telomere fluorescence of sister chromatids appeared to be of similar intensity (FIGS. 1A and 1C), an impression that was confirmed by image analysis (FIGS. 2 and 3). For quantification purposes digital images from metaphase chromosomes after hybridization with the PNA probe and counter staining with propidium iodide (PI) were captured using a CCD camera (see description of image collection and analysis above). An example of this analysis is shown in FIG. 2 and Table 1.

In particular, Table 1 shows the heterogeneity in telomere fluorescence signals from individual chromosomes of a single metaphase. CCD camera images of telomere fluorescence in situ hybridization (FISH) on a metaphase spread of a cultured fetal liver cell (shown in FIG. 2 and used for image analysis as described above for FIG. 2). The fluorescence intensity of individual telomeres (expressed in arbitrary units) is shown for the 26 chromosomes (arbitrary numbers) indicated in FIG. 2. Note the heterogeneity in fluorescence per telomere (i.e. compare data for chromosome 11, spot 1–2=highest average telomere fluorescence, with chromosome 20, spot 3–4=lowest average telomere fluorescence; ratio 11.1–2/20.3–4=5.9 ) and in the total telomere fluorescence per chromosome (i.e. fluorescence per chromosome (i.e. total fluorescence chr 11/chr 9=2.8).

Table 1 and FIG. 2 illustrate that within the individual metaphase considerable heterogeneity in fluorescence per telomere and in total telomere fluorescence per chromosome are observed.

When telomere fluorescence values of all the chromosomes analyzed in this study (n=1273) were analyzed, a good correlation between the values derived from sister chromatid telomere pairs was observed. In particular, FIG. 3 shows graphs correlating telomere fluorescence of sister chromosomes in metaphase chromosomes. The fluorescence intensity of individual telomere spots on all chromosomes analyzed in this study (n-1273, from hematopoietic cell cultures of fetal liver, cord blood, bone marrow and chronic myeloid leukemia cells) were ranked in two sister chromatid pairs corresponding to their location on the chromosome (pair 1: spot 1–spot 2; pair 2: Spot 3–spot 4). The fluorescence intensity of all spots was comparable (mean±s.d., spot 1: 564±273; spot 3: 567±288; spot 4: 563±279) but was significantly better correlated between sister chromatid pairs than between telomeres on opposite ends of the chromosome (correlation coefficients: spot 1–spot 2=0.71; spot 1–spot 3=0.35; spot 2–spot 3=0.34; spot3–spot 4=0.72; spot 1–spot 4=0.33; spot 2–spot 4=0.33; spot 1+2–spot 3+4=0.39).

Figure 4:
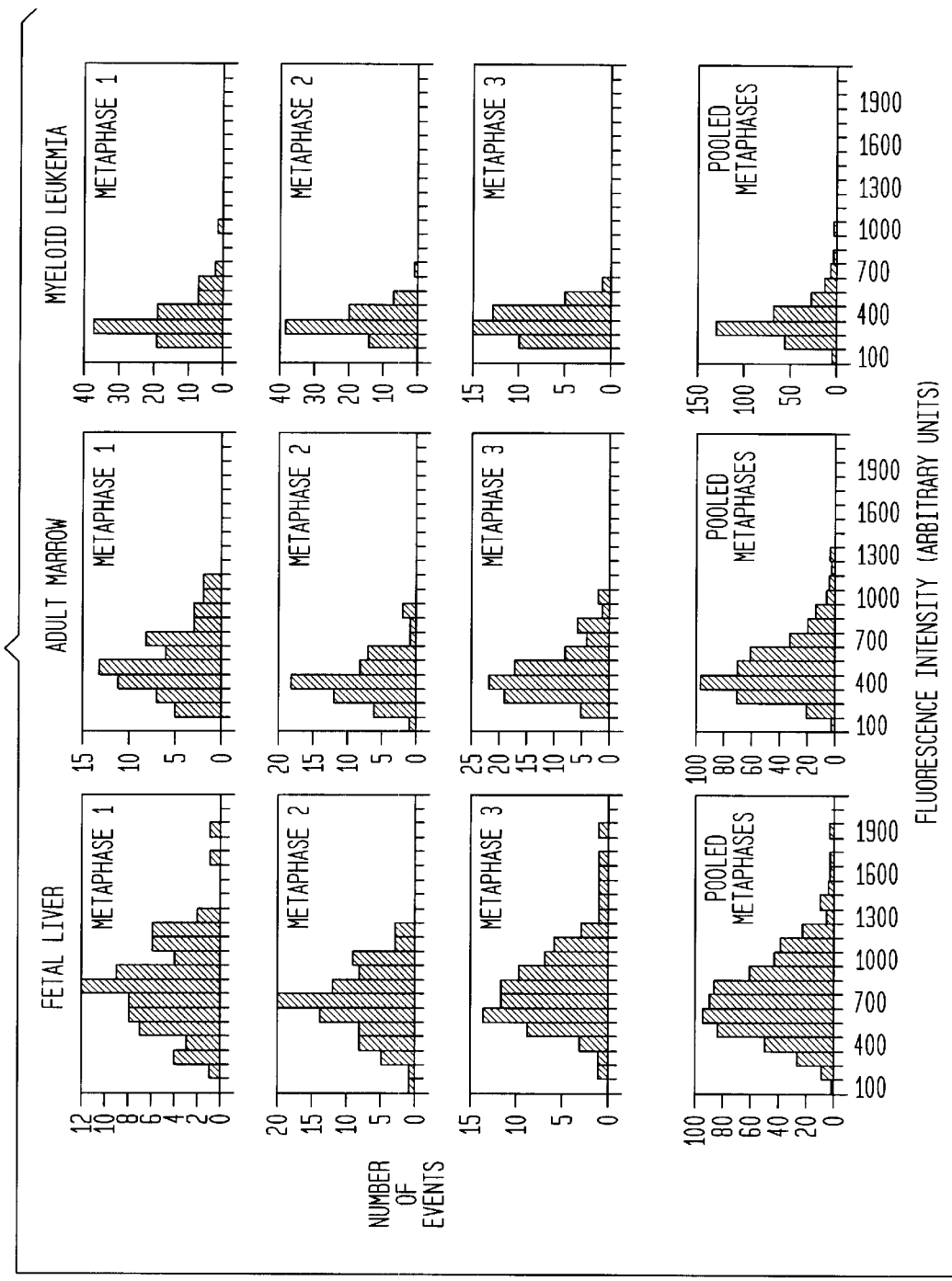
FIG. 4 are graphs showing the distribution of telomere fluorescence intensity on metaphase chromosomes from different tissues.

Striking differences in fluorescence intensity of telomeres in cells from fetal liver, adult bone marrow and chronic myeloid leukemia cells were observed. FIG. 4 are graphs showing the distribution of telomere fluorescence intensity on metaphase chromosomes from different tissues. Telomere fluorescence (in arbitrary units) was calculated from digital images as described above for FIG. 2 and in the description of image analysis above. Values for telomere fluorescence (4/chromosome) within the indicated range are shown for 3 different individual metaphases (numbers corresponding to those in Table 2) as well as the pool of all chromosomes analyzed from each slide/tissue. Note that the distribution of telomere fluorescence within an individual metaphase corresponds well to the overall distribution within the pool of metaphase chromosomes of each tissue and that this distribution is not symmetrical particularly so in chromosomes of normal adult bone marrow and chronic myeloid leukemia cells.

Table 2 shows heterogeneity in telomere length on chromosomes from different hematopoietic tissues. Metaphase preparations from the indicated tissues were hybridized with the PNA-telomere probe and the fluorescence intensity of individual telomeres as well as whole chromosomes (sum of four telomere spots) were measured from digital images described above for FIG. 2. The results shown are from individual slides that contained metaphases with at least 10 chromosomes that could be analyzed (i.e. non-overlapping, correct segmentation, four spots). The same fixed bone marrow cells were used to prepare two different slides. Min-max values for telomere fluorescence were obtained by averaging the sum of two sister chromatid telomere values.

Several points are worth noting from this data. First independent of the tissue analyzed, telomere fluorescence values varied to a greater extent between chromosomes than was anticipated from the data of flow sorted chromosomes reported by Moyzis (R. K. Moyzis, et al., Proc. Natl. Acad. Sci. U.S.A. 85:6622, 1988). Within individual metaphases, the total telomere signal was found to vary up to 3-fold per chromosome and up to 6-fold per telomere. The minimum telomere fluorescence values (expressed on a linear scale and presumably linearly related to the number of $T_2AG_3$ repeats) were found to differ less than 2-fold between the various tissues (Table 2). The latter suggests that a threshold or minimum number of $T_2AG_3$ repeats is required for telomere function. This notion is compatible with studies of telomeres in yeast (E. H. Blackburn, Cell 77:621, 1994 and L. L. Sandell, and V. A. Zakian, Cell 75:729, 1993) and the observation that immortal tumour cells express high levels of functional telomerase (N. W. Kim, et al., Science 266:2011, 1994). Secondly, the variation between fluorescence intensity values from different metaphases on the same slide and between slides (BM-1 versus BM-2) appears relatively small (Table 2 and FIG. 4). Together with the observed linkage of sister chromatid telomere fluorescence (FIG. 3), this observation underscores the notion that the PNA-FISH protocol described herein approaches 100% efficiency for the detection of $T_2AG_3$ repeats. Finally, the distribution of telomere fluorescence appears to be non-random, particularly so in metaphases derived from normal bone marrow and chronic myeloid leukemia cells (FIG. 4). In normal adult bone marrow cells this non-random distribution may be the result of in vivo selection of cells that avoided postulated critical telomere shortening (C. B. Harley et al., Exp. Gerontol. 27:375, 1992 and 20) or, alternatively, a selective action of telomerase on chromosomes with short telomeres. This latter hypothesis is compatible with the recent observation that telomerase activity in yeast is negatively regulated by telomere length and internal telomeric repeat sequences (D. R. Howard et al., J. Immunol. 136:4013, 1986) as well as the presence of measurable telomerase activity in normal bone marrow cells. Based on the observations shown in FIG. 4 and Table 2 and these considerations, it appears that telomerase activity in normal hematopoietic cells is restricted to chromosomes with short telomeres resulting in continuous replication-dependent shortening of long telomeres and the maintenance of short telomeres. Careful analysis of telomere fluorescence from individual chromosomes in clonally propagated normal cells from different tissues using the PNA-FISH technology described here could be used to test this hypothesis. This approach makes it possible to determine whether differences in telomere length are randomly distributed among chromosomes in cells from different tissues.

Example 2

Protocol for Flow FISH

The method of the invention to detect and/or quantitate telomere repeats may be adapted to detect and/or quantitate telomere repeats in nucleic acids in individual cells in suspension. A proposed protocol is as follows. Cells are harvested and washed in phosphate buffered saline (PBS) by centrifuging in a microfuge (30 seconds at 5000 g), and resuspended in a known volume of PBS. The cells are counted using Trypan Blue, and the viability of the cells is recorded (total cell number live+dead). The cells are distributed over Eppendorf tubes up to $4 \times 10^7$ per tube, PBS is added, and the mixture is centrifuged in a microfuge. The pellet is resuspended in PFX™-A (Caltag Fixation & Permeabilization reagent) (max–$10^7$cells/200 µl PFX), mixed, and incubated for 15 minutes at room temperature. PBS is added, and the mixture is centrifuged in a microfuge. The pellet is resuspended in the PFX-B (same volume and cell numbers as for PFX-A), incubated for 10 min RT, PBS is added, and the mixture is centrifuged in a microfuge. The pellet is resuspended in 200 µl PBS per $10^7$cells and mixed well. RNAseA (from@500µg/ml stock in glycerol—Sigma) is added to a final concentration of 10 µg/ml - - - 1:50, mixed and incubated for 30 min in 37° C. (water bath) with occasional shaking. PBS is added and the tubes are centrifuged in a microfuge. The pellet is resuspended in 200 µl/$10^7$ cells acidified water, pH=2 +pepsin [frozen (−20° C.) stock in PBS @ 50 mg/ml—Sigma] at a final concentration 0.5 mg/ml - - - 1:100. Pepsin is thawed just before making a working solution, and it is added to the cells. After adding pepsin, the tubes are put on ice, and then transferred to a 37° C. waterbath. The tubes are incubated 10 min, put on ice, 1 ml of PBS is added, and they are centrifuged in a microfuge. The pellet is resuspended in 200 µl (per $10^7$ cells) of PFX-A, max–$2 \times 10^7$ cells/400 µl, mixed well, and incubated for 15 minutes at room temperature. PBS is added to the top and the tubes are centrifuged in a microfuge. The pellet is resuspended in 200 µl (per $10^7$ cells) of PFX-B, max–$2 \times 10^7$ cells/400 µl, mixed well and incubated for 5 minutes at room temperature. PBS is added, and the tubes are centrifuged in a microfuge. One more wash is carried out with PBS, and the pellet is resuspended in PBS, and divided over Eppendorf tubes for the required number of samples (e.g. no-probe, c-myc, tel, etc.). PBS is added, and the tubes are centrifuged in a microfuge. The supernatant is almost completely removed with a needle suction leaving max~10–20 µl over the pellet. The hybridization mixture is added and the mixture is mixed well with the Eppendorf tip. The maximum cell number per 100 µl mixture is about $2 \times 10^6$ and the maximum volume in a tube should not exceed 500 µl. The minimal volume of hybridization mixture added per sample is about 200 µl. The tubes are left in RT for 10 min, and placed in a Thermomixer set up to 87° C. (the actual temperature inside a tube is ~80° C.) for 10 min shaking. The tubes are incubated in RT overnight (~17 hrs) protected from light. The tubes are centrifuged (Beckman centrifuge at maximum RPMI for 7 min) and the supernatant is removed.

The pellets are vortexed well before adding washing solution, and they are vortexed again after adding the washing solution. It is recommended that the samples stay in RT for ~10 min between all the washes. Two washings are carried out with 1 ml 70% formamide/0.1% BSA/ 0.1%Tween 20 and centrifuging in a Beckman centrifuge at maximum RPMI for 7 min. Three washings are then carried out with 1 ml TNTB (Tris/NaCl/0.1% TWEEN™20/ 0.1%BSA) and centrifuging in a Beckman centrifuge. The first TNTB wash is at maximum RPMI for 7 min, the second is at 1800 PRPMI for 6 min, and the third washing is at 1500 RPMI for 5 min. The pellet is resuspended in PBS+7AAD @0.25 µg/ml final (FACSort) or DAPI@ 0.05 µg/ml final (FACStar+). About 20 µl of cells is left in each tube for counting. The cell recovery is recorded. The samples are analyzed with a linear amplification for all FACS parameters. The instrument setting and mean channel fluorescence is recorded for all the samples.

Example 3

Figure 5:
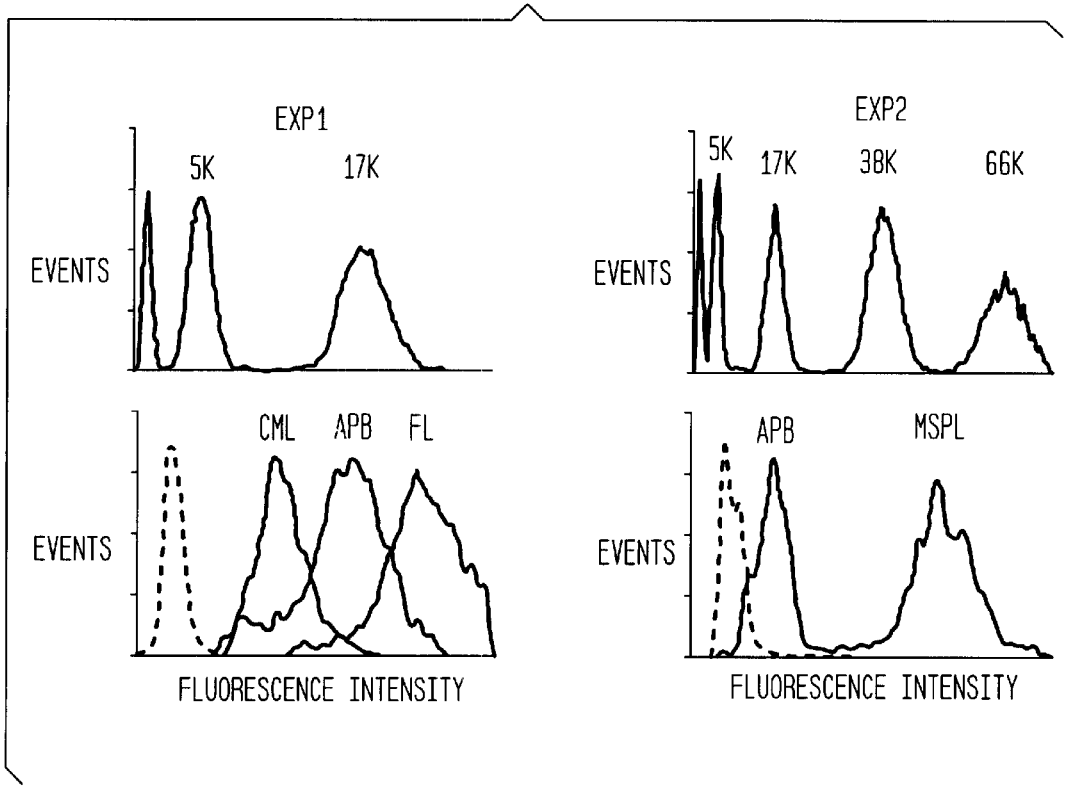
FIG. 5 shows flow histograms of calibration beads (top) and the indicated cell types (bottom) after suspension PNA hybridization with telomere probe (solid lines) and a control probe (c-Myc, dashed lines)

Preliminary data indicate that quantitative telomere measurements in interphase cells are possible (FIG. 5). FIG. 5 shows flow histograms of calibration beads (top) and the indicated cell types (bottom) after suspension PNA hybridization with telomere probe (solid lines) and a control probe (c-Myc, dashed lines). These preliminary results were obtained with Permeafix™ fixed cells, after RNAse and pepsin treatment and hybridization with FITC-labeled $(C_3TA_2)_3$ PNA. Note that nuclei of mouse spleen cells (MSPL) have a 3-fold increased fluorescence relative to human adult peripheral blood (APB) cells and that human fetal liver (FL) cells show a brighter telomere signal than adult blood and chronic myeloid leukemia (CML) cells.

In the preliminary studies variables known or expected to be important for suspension in situ hybridization were systematically explored. The effect of a number of variables on the specific and non-specific hybridization of PNA probes to different human cell types was examined. For this purpose, FITC-labeled PNA specific for telomeric $T_2AG_3$ DNA and a single copy gene such as the c-Myc-gene respectively was used. Variables that were investigated include: 1) fixation; 2) permeabilization; 3) proteolytic digestion; 4) denaturation and 5) hybridization. Because all these variables are to a large extent interdependent, the selected protocol and concentrations of reagents represents only an example of a workable protocol. The variables that were tested are listed in Table 3.

The protocol development efforts resulted in cells/nuclei with 92 fluorescent spots in interphase (46 chromosomes, 2 telomeres each). Unlike metaphase chromosomes, these fluorescence signals will not be captured efficiently in a single plane. Harvesting fluorescence from multiple focal planes may be achieved using confocal microscopy. This possibility has been examined using suboptimal hybridized nuclei on two different confocal microscopes (one at UBC, Vancouver, Canada, and one at the Fred Hutchinson Cancer Research Center in Seattle). Relative to deconvolution fluorescence microscopy, the studies showed poor resolution and/or detection of telomere-specific fluorescence signals probably due to bleaching of the signals due to the high intensity laser light. Better results in terms of spatial resolution, bleaching and detection sensitivity were obtained using optical sectioning fluorescence microscopes from Applied Precision (Hiraoka Y. et al., Biophys J. 57:325–333, 1990); instrumentation at the Fred Hutchinson Cancer Research Center in Seattle) and the system described by Fay et al. (Carrington W A et al., Science 268:1483–1487, 1995).

Example 4

Fluorescence Intensity Correlates with Number of T₂AG3 Repeats in Plasmids

Figure 6:
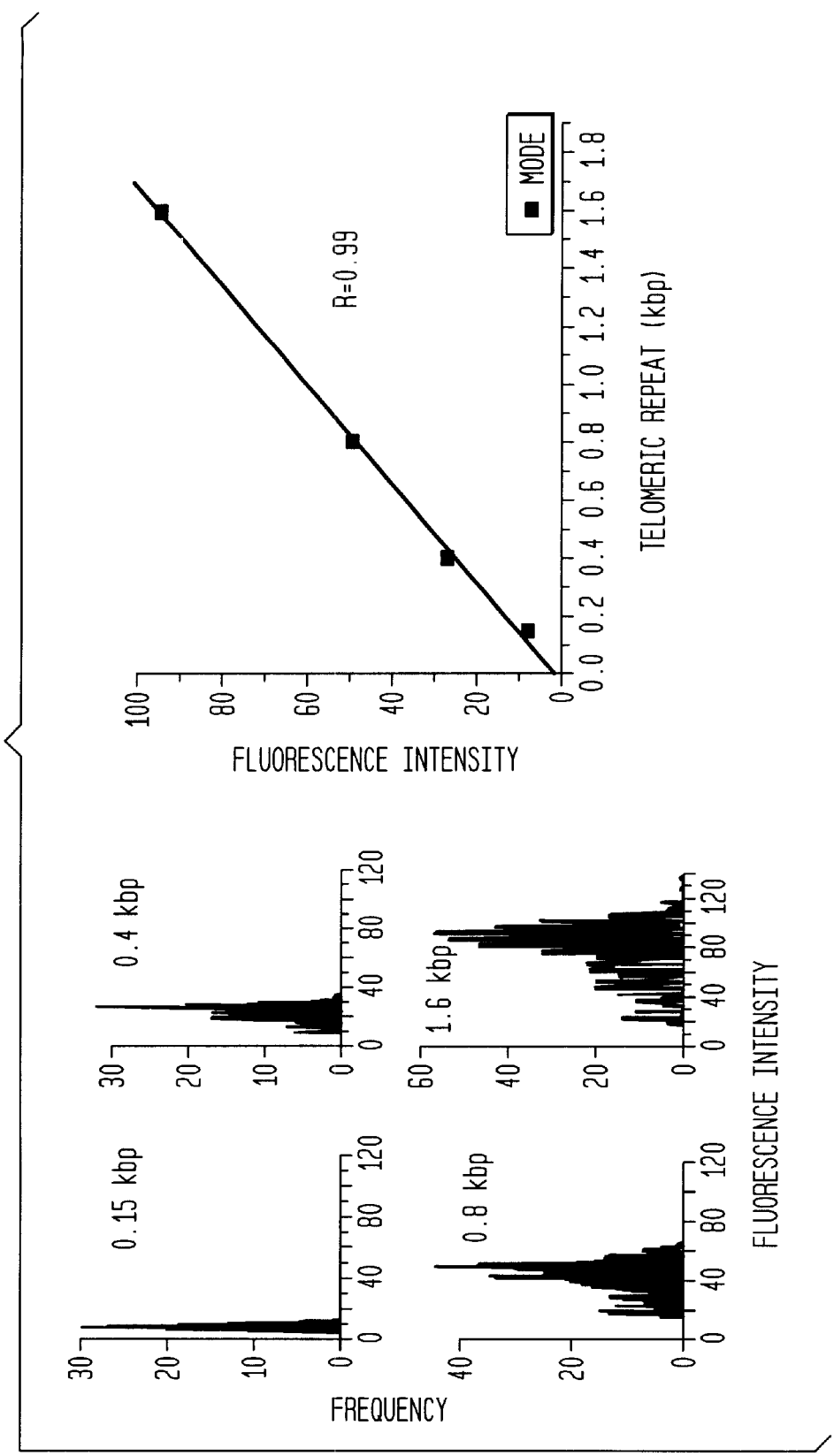
FIG. 6 are histograms and a graph showing that fluorescence spot intensity after hybridization with fluorescently labeled telomere PNA probe correlates with the length of $T_2AG_3$ inserts in plasmids.

Telomere fluorescence intensity values were found to correlate well with terminal restriction fragment size (FIG. 6) and, more strikingly, with actual size of $T_2AG_3$ repeats in recent PNA-FISH experiments with purified plasmids (containing $T_2AG_3$ repeat inserts of 0.2, 0.4, 0.8, and 1.6 kb, respectively; plasmids obtained from Dr. Titia de Lange, Rockefeller University, New York) as is shown in FIG. 6. FIG. 6 shows fluorescence spot intensity after hybridization with fluorescently labeled telomere PNA probe correlates with the length of $T_2AG_3$ inserts in plasmids.

From these experiments, it is concluded that the median fluorescence intensity obtained by image analysis from PNA-FISH chromosomes can be used to estimate the length of $T_2AG_3$ repeats.

However, the fluorescence intensity distribution in FIG. 6 also shows that not all plasmids of a given size yield an identical fluorescence intensity value. Possible explanations include—biological-variables such as loss of DNA during the hybridization procedure and/or conformational changes of target DNA that are incompatible with PNA hybridization. Such variables can be superimposed on the measurement (instrument/image analysis) related variability that are known from experiments with calibration beads to account for errors up to 30–40%. For these reasons, measurements are repeated for 15–25 metaphases per cell type to yield acceptable histograms (see i.e., FIG. 6). The mean fluorescence intensity from such histograms is then used to calculate the mean telomere length on that chromosome arm in the cells used to prepare that slide.

While what is shown and described herein constitutes various preferred embodiments of the subject invention, it will be understood that various changes can be made to such embodiments without departing from the subject invention, the scope of which is defined in the appended claims.

TABLE 1

| chr nmbr | Pair 1 | | Pair 2 | | sum |
| --- | --- | --- | --- | --- | --- |
| | spot 1 | spot 2 | spot 3 | spot 4 | |
| 1 | 698 | 340 | 651 | 622 | 2311 |
| 2 | 306 | 334 | 642 | 583 | 1865 |
| 3 | 347 | 293 | 727 | 548 | 1915 |
| 4 | 546 | 957 | 1154 | 826 | 343 |
| 5 | 393 | 631 | 609 | 675 | 2308 |
| 6 | 478 | 464 | 408 | 581 | 1931 |
| 7 | 485 | 431 | 562 | 435 | 1916 |
| 8 | 1071 | 717 | 742 | 923 | 3453 |
| 9 | 401 | 357 | 633 | 386 | 1783 |
| 10 | 617 | 1015 | 705 | 657 | 2994 |
| 11 | 1648 | 1355 | 507 | 372 | 3882 |
| 12 | 442 | 483 | 400 | 393 | 1718 |
| 13 | 928 | 584 | 383 | 567 | 2462 |
| 14 | 712 | 568 | 462 | 359 | 2101 |
| 15 | 765 | 529 | 432 | 430 | 2156 |
| 16 | 782 | 892 | 1092 | 964 | 3730 |
| 17 | 454 | 307 | 615 | 384 | 1760 |
| 18 | 760 | 405 | 689 | 685 | 2539 |
| 19 | 398 | 373 | 735 | 521 | 2027 |
| 20 | 378 | 405 | 262 | 344 | 1389 |
| 21 | 756 | 505 | 774 | 683 | 2713 |
| 22 | 312 | 496 | 409 | 407 | 1624 |
| 23 | 298 | 359 | 527 | 471 | 1655 |
| 24 | 555 | 479 | 456 | 410 | 1900 |
| 25 | 641 | 700 | 765 | 475 | 2581 |
| 26 | 701 | 774 | 1085 | 501 | 3061 |

TABLE 2

| Tissue | Metaphase | # Chromosomes | Chromosome Values | | | | | Telemere Values | | | | |
|---|---|---|---|---|---|---|---|---|---|---|---|---|
| | | | Min | Max | Ratio | Mean | S.D. | Min | Max | Ratio | Mean | S.D. |
| FL | 1 | 18 | 1405 | 5796 | 4.12 | 3101 | 980 | 299 | 1443 | 4.82 | 806 | 264 |
| | 2 | 23 | 1228 | 4116 | 3.35 | 2603 | 605 | 210 | 1137 | 5.41 | 628 | 198 |
| | 3 | 21 | 1466 | 4900 | 3.34 | 3050 | 797 | 360 | 1770 | 4.91 | 764 | 253 |
| | 4 | 24 | 1602 | 4059 | 2.53 | 2861 | 682 | 295 | 1449 | 4.9 | 692 | 226 |
| | 5 | 14 | 2019 | 3738 | 1.85 | 2971 | 492 | 386 | 1144 | 2.96 | 738 | 167 |
| | 6 | 18 | 1475 | 4028 | 2.73 | 2735 | 807 | 191 | 1234 | 6.45 | 682 | 224 |
| | 7 | 19 | 1273 | 3548 | 2.78 | 2224 | 569 | 267 | 978 | 3.66 | 542 | 181 |
| | 8 | 11 | 2078 | 4277 | 2.05 | 2842 | 796 | 349 | 1117 | 3.2 | 716 | 250 |
| | Pool | 148 | 1568 | 4307 | 2.84 | 2798 | 715 | 294 | 1284 | 4.53 | 695 | 220 |
| BM-1 | 1 | 15 | 974 | 3233 | 3.31 | 1948 | 726 | 166 | 901 | 5.43 | 487 | 202 |
| | 2 | 14 | 1015 | 2463 | 2.42 | 1493 | 431 | 106 | 686 | 6.44 | 367 | 141 |
| | 3 | 12 | 1311 | 2808 | 2.14 | 1727 | 432 | 249 | 943 | 3.78 | 431 | 146 |
| | 4 | 20 | 1081 | 2716 | 2.51 | 1702 | 543 | 221 | 781 | 3.53 | 429 | 154 |
| | 5 | 18 | 1083 | 4019 | 3.71 | 2006 | 708 | 201 | 1277 | 6.36 | 498 | 221 |
| | 6 | 16 | 1540 | 3007 | 1.95 | 1972 | 407 | 237 | 840 | 5.53 | 472 | 128 |
| | Pool | 95 | 1167 | 3041 | 2.67 | 1808 | 541 | 197 | 905 | 4.84 | 449 | 165 |
| BM-2 | 1 | 14 | 1285 | 3157 | 2.45 | 1958 | 671 | 254 | 992 | 3.91 | 467 | 168 |
| | 2 | 24 | 1372 | 3778 | 2.75 | 2180 | 719 | 209 | 1074 | 5.12 | 522 | 217 |
| | 3 | 11 | 1328 | 2690 | 2.03 | 2054 | 418 | 263 | 835 | 3.17 | 477 | 138 |
| | 4 | 14 | 767 | 2770 | 3.61 | 1822 | 631 | 139 | 942 | 6.78 | 456 | 224 |
| | 5 | 17 | 1175 | 3098 | 2.63 | 1783 | 468 | 219 | 919 | 4.19 | 433 | 142 |
| | 6 | 13 | 811 | 2763 | 3.41 | 1921 | 538 | 277 | 712 | 4.2 | 465 | 178 |
| | 7 | 10 | 874 | 2915 | 3.33 | 1605 | 697 | 174 | 867 | 4.97 | 401 | 221 |
| | Pool | 103 | 1087 | 3024 | 2.88 | 1903 | 591 | 205 | 906 | 4.59 | 460 | 184 |
| CML | 1 | 23 | 886 | 2144 | 2.41 | 1306 | 350 | 161 | 845 | 5.25 | 308 | 128 |
| | 2 | 12 | 1041 | 1953 | 1.88 | 1391 | 319 | 174 | 769 | 4.41 | 343 | 142 |
| | 3 | 20 | 943 | 1872 | 1.98 | 1163 | 229 | 172 | 412 | 2.4 | 283 | 69 |
| | 4 | 11 | 751 | 1448 | 1.93 | 1052 | 255 | 157 | 476 | 3.03 | 273 | 88 |
| | Pool | 66 | 905 | 1854 | 2.05 | 1227 | 288 | 166 | 625 | 3.77 | 301 | 106 |

TABLE 3

Variables in the development of suspension FISH.

| Fixative | Reference |
|---|---|
| Paraformaldehyde | Arkesteijn GJA, et al Cytometry 19: 353–360, 1995, and Brady G, et al. Curr Biol 5: 909–922, 1995. |
| Formaldehyde | Ravichandran KS, et al. J Immunol Methods 153: 249–259, 1992. |
| Ethanol | van Dekken H, et al. Cytometry 11: 153–164, 1990. |
| Streck Tissue Fixative | Patterson BK, et al. Science 260: 976–979, 1993. |
| Permeafix ™ | Studies herein |
| Permeabilization | |
| Triton-X600 | Arkesteijn GJA, et al Cytometry 19: 353–360, 1995, Hoy CA et al.. Cytometry 10: 718–725, 1989. |
| SDS | Wallner G, et al. Cytometry 14: 136–143, 1993. |
| Tween | van Dekken H, et al. Cytometry 11: 153–164, 1990; Ravichandran KS, et al. J Immunol Methods 153: 249–259, 1992. |
| Proteolytic Digestion | |
| Proteinase K | Patterson BK, et al. Science 260: 976–979, 1993 |
| Trypsin | Arkesteijn GJA, et al. Cytometry 19: 353–360, 1995. |
| Pepsin | |
| Denaturation | |
| Temperature | Arkesteijn GJA,et al. Cytometry 19: 353–360, 1995; Hoy CA et al., Cytometry 10: 718–725, 1989 |
| 0.1 M HCl | van Dekken H, et al. Cytometry 11: 153–164, 1990. |

I claim:

1. A method for detecting multiple copies of a repeat sequence in a nucleic acid molecule in morphologically intact chromosomes, cells, or tissue sections comprising: (a) treating the nucleic acid molecule with a PNA probe which hybridizes to a repeat sequence in the nucleic acid molecule and which is labeled with a detectable substance, under denaturing conditions utilizing a denaturing agent, permitting the probe to hybridize in situ to the repeat sequence in the nucleic acid molecule; and (b) identifying said probe hybridized to the repeat sequence in the nucleic acid molecule by directly or indirectly detecting the detectable substance, thereby detecting the multiple copies of a repeat sequence in a nucleic acid molecule.

2. The method of claim 1, wherein the detectable substance is a fluorophore, isotope, or chemiluminescent compound.

3. The method of claim 1, wherein the detectable substance is a fluorophore, and the identifying step comprises forming an image of the hybridized probe and detecting fluorescence in the image.

4. The method of claim 1, wherein the detectable substance is an enzyme or a hapten.

5. A method for quantitating the length of multiple copies of a repeat sequence in a nucleic acid molecule in morphologically preserved chromosomes, cells or tissue sections, comprising:
   (a) treating the nucleic acid molecule with a PNA probe that is labeled with a detectable substance, wherein the probe hybridizes to the repeat sequence in the nucleic acid molecule, under denaturing conditions, utilizing a denaturing agent, permitting the probe to hybridize in situ to the repeat sequence in the nucleic acid molecule;
   (b) identifying probe hybridized to the repeat sequence in the nucleic acid molecule by detecting a signal produced directly or indirectly by the detectable substance; and
   (c) quantitating the length of the multiple copies of the repeat sequence in the nucleic acid molecule based on the direct relationship between the intensity of the signal produced directly or indirectly by the detectable substance and the length of the multiple copies of the repeat sequence.

6. The method of claim 5, wherein the repeat sequence is a telomere or centromere repeat sequence.

7. The method of claim 6, wherein the repeat sequence is TTAGGG and the PNA probe contains the sequence CCCTAA.

8. The method of claim 6, wherein the telomere repeat sequence is a human telomere repeat sequence.

9. A method for quantitating the length of multiple copies of a telomere repeat sequence TTAGGG or CCCTAA, in a nucleic acid molecule in morphologically preserved chromosomes, cells or tissue sections comprising:
(a) treating the nucleic acid molecule, in the presence of a blocking reagent and a denaturing agent, with a PNA probe comprising the sequence CCCTAA or TTAGGG wherein the probe is labeled with a fluorophore, and permitting the probe to hybridize in situ to the telomere repeat sequence in the nucleic acid molecule;
(b) forming an image of probe hybridized to telomere repeat sequences in the nucleic acid molecule; and
(c) quantitating the length of the telomere repeat sequences in the nucleic acid molecule based on the direct relationship between fluorescence intensity and the length of the multiple copies of the telomere sequence.

10. A method for determining the replicative potential of a cell by quantitating the length of multiple copies of telomere repeat sequence in nucleic acid molecules in the cell comprising:
(a) treating the nucleic add molecules with a PNA probe comprising the sequence CCCTAA or TTAGGG that is labeled with a detectable substance, wherein the probe hybridizes to TTAGGG or CCCTAA telomere repeat sequences in the nucleic acid molecules, under denaturing conditions utilizing a denaturing agent, permitting the probe to hybridize in situ to the telomere repeat sequences in the nucleic acid molecules;
(b) identifying probe hybridized to the telomere repeat sequences in the nucleic acid molecule by detecting a signal produced directly or indirectly by the detectable substance;
(c) quantitating the length of the multiple copies of the telomere repeat sequence based on the direct relationship between the intensity of the signal produced directly or indirectly by the detectable substance and the length of the multiple copies of the telomere repeat sequence; and
(d) determining the replicative potential by comparing the quantitated length of the multiple copies of the telomere repeat sequence with the length of multiple copies of the telomere repeat sequence associated with cells having a known replicative potential.

11. A method for determining the effect of a substance on telomerase activity comprising:
(a) treating cells having telomerase activity with:
(i) a PNA probe comprising the sequence CCCTAA or TTAGGG that is labeled with a detectable substance, wherein the probe hybridizes to TAGGG or CCCTAA telomere repeat sequences, under denaturing conditions utilizing a denaturing agent, permitting the probe to hybridize in situ to the TTAGGG or CCCTAA telomere repeat sequences in nucleic add molecules in the cells; and
(ii) a substance suspected of affecting telomerase activity;
(b) identifying probe hybridized to TTAGGG or CCCTAA telomere repeat sequences in the nucleic acid molecules by detecting a signal produced directly or indirectly by the detectable substance;
(c) quantitating the length of the multiple copies of the TTAGGG or CCCTAA telomere repeat sequence based on the direct relationship between the intensity of the signal produced directly or indirectly by the detectable substance and the length of the multiple copies of the telomere repeat sequence; and
(d) determining the effect of the substance on telomerase activity by comparing the results of step (c) with cells treated without the substance.

12. A method for quantitating the length of multiple copies of repeat sequences in nucleic acid molecules in cells in suspension comprising:
(a) treating morphologically preserved cells with a PNA probe that is labeled with a detectable substance, wherein the probe hybridizes to the repeat sequence in the nucleic acid molecule, under denaturing conditions utilizing a denaturing agent, permitting the probe to hybridize in situ to the repeat sequences in the nucleic acid molecule;
(b) subjecting the treated cells to flow cytometry or image cytometry to detect the detectable substance and produce a signal corresponding to the amount of probe hybridized to repeat sequences in the nucleic add molecule; and
(c) quantitating the length of the multiple copies of the repeat sequences in the nucleic acid molecule based on the relationship between the intensity of the signal and the length of the multiple copies of the repeat sequence.

13. The method of claim 12, wherein the repeat sequence is a telomere repeat sequence.

14. The method of claim 13, wherein the telomere repeat sequence is TTAGGG and the probe contains the sequence CCCTAA.

15. The method of claim 12, wherein the detectable substance is a fluorophore.

16. The method of claim 13, wherein the cells are lymphocytes.

17. A method for distinguishing normal cells from tumor cells in a cell suspension containing normal cells and tumor cells comprising:
(a) treating morphologically preserved cells with a PNA probe that is labeled with a detectable substance, wherein the probe hybridizes to multiple copies of a repeat sequence in nucleic acid molecules in the cells under denaturing conditions utilizing a denaturing agent, permitting the probe to hybridize in situ to the repeat sequences in the nucleic acid molecules in the cells;
(b) subjecting the treated cells to flow cytometry or image cytometry to detect the detectable substance and produce a signal corresponding to the quantity of probe hybridized to repeat sequences in the nucleic acid molecule; and
(c) determining whether the cells are normal cells or tumor cells by comparing the signal with a signal obtained for known normal cells or tumor cells.

18. The method of any one of claims 5, 10, 12, or 17, wherein the detectable substance is a fluorophore, isotope, or chemiluminescent compound.

19. The method of any one of claims 5, 10, 12, or 17, wherein the detectable substance is an enzyme or hapten.

* * * * *